United States Patent [19]
Wiltrout et al.

[11] Patent Number: 5,637,323
[45] Date of Patent: Jun. 10, 1997

[54] METHOD OF MOBILIZING PLURIPOTENTIAL HEMATOPOIETIC STEM CELLS WITH IL-7

[75] Inventors: Robert H. Wiltrout, Frederick; Francis Ruscetti, New Market; Krzysztof Grzegorzewski, Montgomery Village; Jonathan Keller, Frederick; Kristin L. Komschlies-McConville, Westminister, all of Md.

[73] Assignee: The United States of America as represented by the Department of Health and Human Services, Washington, D.C.

[21] Appl. No.: 341,399

[22] Filed: Nov. 16, 1994

[51] Int. Cl.$^6$ .......................... C12N 15/85; A61K 35/14; A01N 63/00
[52] U.S. Cl. ...................... 424/534; 424/93.71; 424/577; 424/85.2; 530/413
[58] Field of Search .............................. 424/93.71, 534, 424/577; 435/240.2; 530/351, 413

[56] References Cited

PUBLICATIONS

Faltyneck, CR et al. (1992). J. of Immunology. vol. 149 pp. 1276–1282.

Murphy WJ. et al. (1993). J. of Clinical Investigation. vol. 92 pp. 1918–1924.

Grzegorzewski et al., Administration of Recombinant Human Interleukin–7 to Mice Induces the Exportation of Myeloid Progenitor Cells From the Bone Marrow to Peripheral Sites, *Blood*, vol. 83, No. 2, pp. 377–385 (Jan. 15, 1994).

Grzegorzewski et al., rhIL7 Induces Extramedullary Hematopoiesis in Mice through the Exportation of Myeloid Progenitor Cells from the Bone Marrow to Peripheral Sites, *J. Cell. Biochem. Suppl.*, Keystone Symposium 17B:63 (Jan. 31, 1993).

Damia et al., Administration of Recombinant Human IL-7 Alters the Frequency and Number of Myeloid Progenitor Cells in the Bone Marrow and Spleen of Mice, *Blood*, vol. 79, No. 5, pp. 1121–1129 (Mar. 1, 1992).

Morrissey et al., Administration of IL-7 to Mice with Cyclophosphamide–induced Lymphopenia Accelerates Lymphocyte Repopulation, *J. Immunol.*, vol. 146, No. 5, pp. 1547–1552 (Mar. 1, 1991).

Jacobsen et al., Novel Role of Interleukin-7 in Myelopoiesis: Stimulation of Primitive Murine Hematopoietic Progenitor Cells, *J. Exp. Med.*, vol. 178, No. 5, pp. 1777–1782 (Nov. 1, 1993).

Jackson et al., Mobilization of Hematopoietic Progenitors Following IL-7 Administration Post–chemotherapy, *Blood*, vol. 82, 10 Suppl. 1, 386A, (Dec. 3, 1993).

Armitage et al., Regulation of Human T Cell Proliferation by IL-7, *J. Immunol.*, vol. 144, No. 3, pp. 938–941, (Feb. 1990).

Alderson et al., Interleukin 7 Enhances Cytolytic T Lymphocyte Generation and Induces Lymphokine–activated Killer Cells from Human Peripheral Blood, *J. Exp. Med.*, vol. 172, pp. 577–587, (Aug. 1990).

Komschlies et al., In Vivo Tumoricidal and Immunohematological Effects of rhIL7 in Mice, *Faseb J.*, vol. 5, No. 6, p. A 1772, Abstract No. 8137 (no date shown).

Komschlies et al., The In Vivo Effects of rhIL7 on T–Cell Number and Function in Normal or Tumor–Bearing Mice, *J. Cell Biochem. Suppl.*, Keystone Symposia on Molecular and Cellular Biology: Cellular Immunity and the Immunotherapy of Cancer, Taos, NM, 17D:133, 1993.

Komschlies et al., Administration of Recombinant Human IL-7 to Mice Alters the Composition of B–Lineage Cells and T Cell Subsets, Enhances T Cell Function, and Induces Regression of Established Metastases, *J. Immunol.*, 152:5776, (1994).

Bensinger et al., Autologous Transplantation With Peripheral Blood Mononuclear Cells Collected After Administration of Recombinant Granulocyte Stimulating Factor, *Blood*, vol. 81, No. 11, pp. 3158–3163, (Jun. 1, 1993).

Anne Kessinger, MD, Utilization of Peripheral Blood Stem Cells in Autotransplantation, *Dept. of Inter. Med.*, University of Nebraska Med. Ctr., Omaha, vol. 7, No. 3, pp. 535–545 (Jun. 1993).

Meagher et al., Techniques of Harvesting and Cryopreservation of Stem Cells, James Graham Brown Cancer Center, University of Louisville (RCM, RHH), and others, vol. 7, No. 3, pp. 501–533 (Jun. 1993).

*Primary Examiner*—Robert D. Budens
*Assistant Examiner*—Julie E. Reeves
*Attorney, Agent, or Firm*—Needle & Rosenberg, PC

[57] ABSTRACT

This invention provides a method of isolating an increased number of hematopoietic stem cells from a subject comprising a) administering interleukin-7 to the subject in an amount that mobilizes the hematopoietic stem cells to the peripheral blood; and, b) isolating a population of leukocytes enriched for hematopoietic stem cells from the peripheral blood. Also provided is a method of transplanting an increased number of hematopoietic stem cells from a donor to a recipient to enhance repopulation of the recipient's hematopoietic and immune cells comprising a) administering interleukin-7 to the donor in an amount that mobilizes the hematopoietic stem cells to the peripheral blood; b) isolating a population of leukocytes enriched for hematopoietic stem cells from the donor's peripheral blood; and, c) transplanting the isolated population of leukocytes enriched for hematopoietic stem cells to the recipient, thereby enhancing the repopulation of the recipient's hematopoietic and immune cells. Finally, the invention provides a method of improving engraftment of a bone marrow transplant or a peripheral blood leukocyte transplant from a donor to a recipient comprising administering interleukin-7 to the recipient following transplantation in an amount that enhances engraftment.

20 Claims, 8 Drawing Sheets

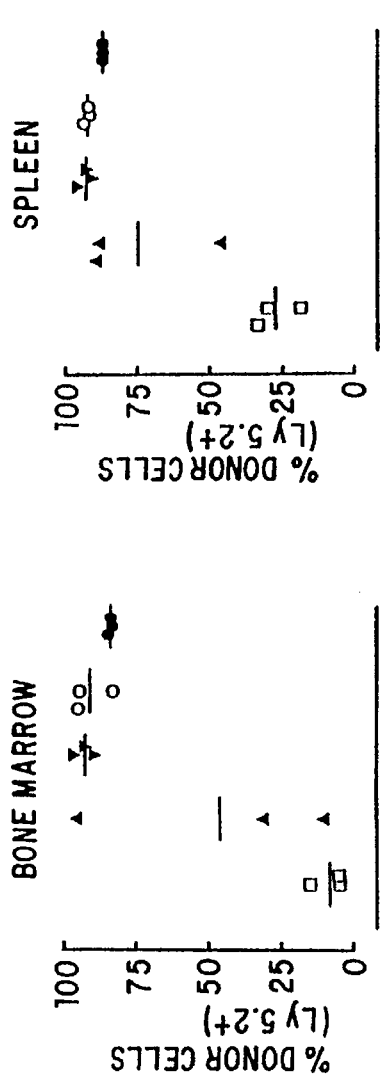
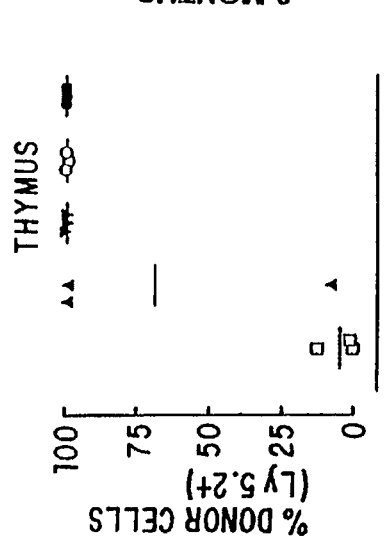
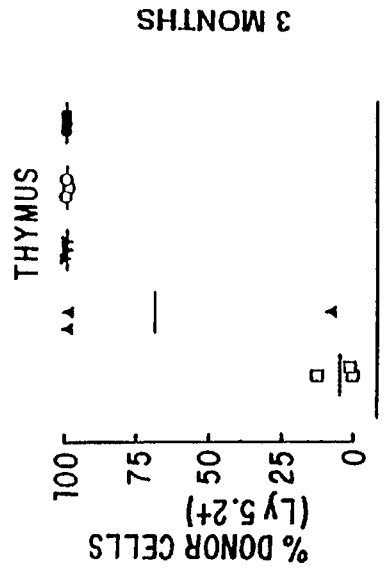
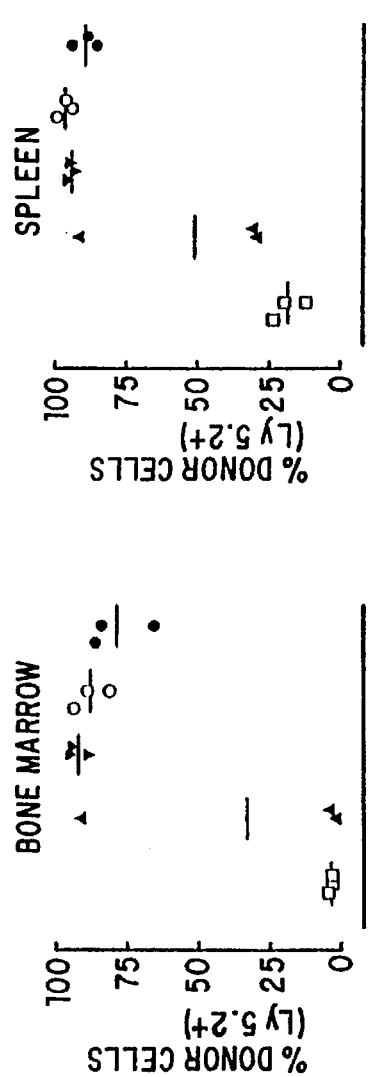
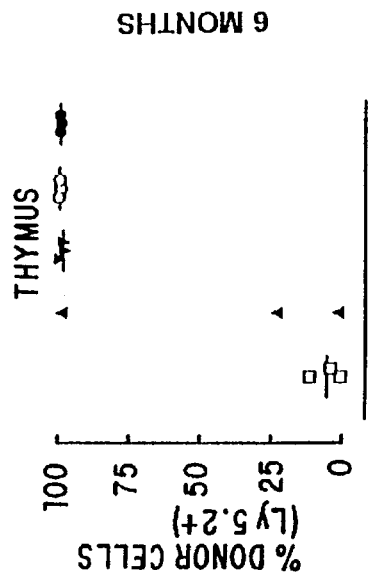
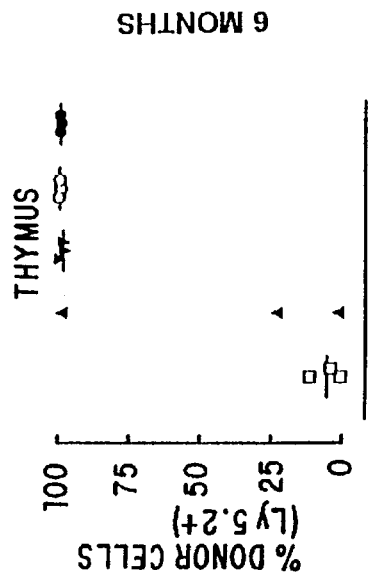

TRI-LINEAGE RECONSTITUTION AT 6 MONTHS IN VARIOUS ORGANS

| GROUPS | BONE MARROW (%Ly 5.2+) | | | SPLEEN (%Ly 5.2+) | | |
|---|---|---|---|---|---|---|
| | 8C5+ | CD3+ | B220+ | 8C5+ | CD3+ | B220+ |
| PWBC (10⁷) CONTROL | 1.4±0.9 | 34.8±7.9 | 11.2±9.1 | 25.3±4.5 | 27.1±3.1 | 13.8±13.0 |
| PWBC (10⁷) rhIL7 | 94.6±4.8 | 89.8±2.3 | 85.9±1.8 | 90.7±4.1 | 89.6±2.5 | 95.5±1.1 |

FIG. 3G

METHOD OF MOBILIZING PLURIPOTENTIAL HEMATOPOIETIC STEM CELLS WITH IL-7

BACKGROUND OF THE INVENTION

1. Field of the Invention

The present invention relates to the field of hematopoietic cell mobilization. In particular, IL-7 has been found to mobilize hematopoietic stem cells, which can be used to augment peripheral blood transfusions and bone marrow transplantations.

2. Background Art

Autologous bone marrow transplantation (BMT) has been used for the support of high dose chemotherapy in the treatment of various neoplastic diseases (1). Under steady-state conditions, the majority of primitive hematopoietic stem and progenitor cells reside in the bone marrow, and only a low number of these cells can be isolated from the peripheral blood. However, additional peripheral blood progenitor cells (PBPC) and peripheral blood stem cells (PBSC) can be mobilized by treatment with myelosuppressive agents (2), and/or certain growth factors (3, 4). Recent studies have shown that PBPC and PBSC exhibit enhanced potential for engraftment as compared to BMT (4, 5).

The differentiation of cells of the various hemopoietic lineages involves a complex and, as yet, incompletely understood series of events. In recent years, advances have been made in isolating and expressing cytokines known to be involved in hematopoiesis. Granulocyte-macrophage-colony stimulating factor (GM-CSF), interleukin-3 (IL-3), granulocyte-CSF, CSF-1 and IL-6 have been shown to be directly stimulatory to myeloid progenitor cells (25, 26). In contrast, the factors which regulate lymphopoiesis at the progenitor cell level are largely unknown despite a large body of evidence showing significant effects of various interleukins on mature T-cells and B-cells.

Several hematopoietic growth factors (I-IGF) have been studied as mobilizing agents, alone or in combination, in preclinical studies or clinical trials (e.g. G-CSF, GM-CSF, IL3/Epo, IL-1, SCF, IL-11) (4, 20). Some HGFs have their activity restricted to myelopoiesis while others stimulate lymphopoiesis and myelopoiesis (21). To date, IL-7 had been reported to primarily stimulate lymphopoiesis (13, 22, 34, 35), with a pronounced increase in the number of mature T lymphocytes, particularly CD8+T-cells, as well as T-cell-mediated responses (13). Additionally, IL-7 has also been found to influence early myeloid progenitors (7). In this regard, IL-7 has been shown to synergize with GM-CSF and SCF to enhance in vitro myeloid colony formation of Lin$^-$Sea-1$^+$ murine BM progenitor cells (9).

Chemotherapy has also been used to mobilize stem cells. The disadvantages of this therapy include the toxicity of chemotherapeutic agents, which can result in neutropenia and sepsis and may lead to death. Additionally, the time consuming nature of the operation is a disadvantage. Mobilization does not occur until approximately 16 days after the chemotherapy is given, 3–6 days are needed for the apheresis procedure, and 2 more weeks must pass to permit the progenitor culture assays to mature. Thus, in a successful mobilization, the entire procedure requires about 5 weeks. Finally, however, the method is not predictably successful. Patients who have already been treated with multiple courses of combination chemotherapy and patients with bone marrow metastases are especially likely to fail chemotherapy-induced mobilization attempts.

The development of a long-term B-lineage culture system allowed the demonstration of sustained lymphopoiesis in vitro (27, 28), whereby populations of pro- and pre-B cells developed over a period of several months. Using this technique, IL-7 was originally described as a bone marrow stromal cell-derived factor that could support the proliferation of B-cell precursors from Whitlock-Witte bone marrow cultures (29), thus demonstrating its growth/regulatory function in lymphopoiesis. Murine and human IL-7 cDNA have both been cloned, sequenced and expressed (30, 31), and there is 60% homology at the amino acid-level. Northern blot analysis of a variety of murine and human tissues showed that the IL-7 gene is transcribed not only in the bone marrow, but also in the spleen and the thymus (30).

IL-7 was thus initially shown to be a B-cell lineage growth factor with preferential stimulating effects on the proliferation of B-cell precursors (30, 32, 33). Subsequently, it was found that IL-7 increased the number of CD3$^+$ cells in bone marrow cultures (22), and also supported the growth of thymocytes (34-36), in particular, the CD4$^-$CD8$^-$, CD4$^+$CD8$^-$ and CD4$^-$CD8$^+$ subsets (37). IL-7 also was shown to act as a co-stimulator for peripheral T-lymphocytes in concert with mitogen or antigen in vitro (38, 39). In vitro, IL-7 has been shown to enhance CSF-induced proliferation of myeloid colony formation (9).

The in vivo effects of IL-7 administration using murine systems also have been examined. Normal mice treated with recombinant murine IL-7 (rmIL-7) have increased lymphocyte numbers (40) and cyclophosphamide-treated mice were able to reconstitute the lymphocyte compartment more rapidly with rmIL-7 treatment (41). Further, administration of recombinant human IL-7 (rhIL-7) to sublethally irradiated mice resulted in accelerated repopulation of T and B lymphocytes and some immature myeloid-lineage cells (8). It has been previously demonstrated that administration of rhIL-7 to mice induced exportation of single-lineage colony-forming units-culture (CFU-c) and multilineage CFU-granulocyte, erythroid, monocyte, and megakaryocyte (CFU-GEMM) colony generating myeloid progenitors from the bone marrow to the spleen that resulted in a 90% decrease in bone marrow myeloid progenitors and a 5-fold increase in the spleen (6, 7). The administration of rhIL-7 has also been shown to result in a 3- to 5-fold leukocytosis in spleen and lymph nodes due to an increase in all major mature leukocytes subsets (B-, T-, NK-cells and macrophages) with a disproportionate increase in pre-B cells and CD8$^+$ T-cells (13). Further, T-cells in rhIL-7 treated mice had enhanced and accelerated abilities to respond to various stimuli (13).

Thus, recent laboratory research has demonstrated that administration of recombinant human interleukin-7 (rhIL-7) to mice mobilized myeloid progenitor cells from the bone marrow to the spleen (6), blood and the liver (7). rhIL-7 treatment does not decrease bone marrow cellularity (6). Administration of rhIL-7 to irradiated mice increased the number of megakaryocytes and immature granulocytes in the spleen in vivo (8). In vitro rhIL-7 enhanced colony stimulating factor-induced myeloid colony formation from primitive Lin$^-$Sca-1$^+$ murine bone marrow progenitor cells, without effecting proliferation of committed Lin$^-$Sca-1$^-$ myeloid progenitors (9). Additionally, researchers have shown the effects of IL-7 on lymphopoiesis (10), and documented the expression of receptors for IL-7 on myeloid cells (11).

However, it has not been shown or suggested that IL-7 can be used to mobilize hematopoietic stem cells to permit isolation of increased numbers of stem cells from the peripheral blood. Such a use of IL-7 would be extremely valuable for use in long term reconstitution in lethally irradiated recipients.

SUMMARY OF THE INVENTION

The present invention provides a method of isolating an increased number of hematopoietic stem cells from a subject comprising a) administering interleukin-7 to the subject in an mount that mobilizes the hematopoietic stem cells to the peripheral blood; and, b) isolating a population of leukocytes enriched for hematopoietic stem cells from the peripheral blood.

The invention also provides a method of transplanting an increased number of hematopoietic stem cells from a donor to a recipient to enhance repopulation of the recipient's hematopoietic and immune cells comprising a) administering interleukin-7 to the donor in an mount that mobilizes the hematopoietic stem cells to the peripheral blood; b) isolating a population of leukocytes enriched for hematopoietic stem cells from the donor's peripheral blood; and, c) transplanting the isolated population of leukocytes enriched for hematopoietic stem cells to the recipient, thereby enhancing the repopulation of the recipient's hematopoietic and immune cells.

The invention also provides a method of improving engraftment of a bone marrow transplant or a peripheral blood leukocyte transplant from a donor to a recipient comprising administering interleukin-7 to the recipient following transplantation in an amount that enhances engraftment.

FIG. 3A shows the percentage of donor cells (Ly $5.1^+$) repopulating the bone marrow of lethally irradiated recipient (Ly $5.2^+$) mice transplanted with PBL and BMC from rhIL-7 or HBSS-treated donors at three months. The results are presented as the mean of 3 mice per group±SD.

FIG. 3B shows the percentage of donor cells (Ly $5.1^+$) repopulating the spleen of lethally irradiated recipient (Ly $5.2^+$) mice transplanted with PBL and BMC from rhIL-7 or HBSS-treated donors at three months. The results are presented as the mean of 3 mice per group±SD.

FIG. 3C shows the percentage of donor cells (Ly $5.1^+$) repopulating the thumus of lethally irradiated recipient (Ly $5.2^+$) mice transplanted with PBL and BMC from rhIL-7 or HBSS-treated donors at three months. The results are presented as the mean of 3 mice per group±SD.

FIG. 3D shows the percentage of donor cells (Ly $5.1^+$) repopulating the bone marrow of lethally irradiated recipient (Ly $5.2^+$) mice transplanted with PBL and BMC from rhIL-7 or HBSS-treated donors at six months. The results are presented as the mean of 3 mice per group±SD.

FIG. 3E shows the percentage of donor cells (Ly $5.1^+$) repopulating the spleen of lethally irradiated recipient (Ly $5.2^+$) mice transplanted with PBL and BMC from rhIL-7 or HBSS-treated donors at six months. The results are presented as the mean of 3 mice per group±SD.

FIG. 3F shows the percentage of donor cells (Ly $5.1^+$) repopulating the thumus of lethally irradiated recipient (Ly $5.2^+$) mice transplanted with PBL and BMC from rhIL-7 or HBSS-treated donors at six months. The results are presented as the mean of 3 mice per group±SD.

FIG. 3G shows multiple-lineage reconstitution determined by the percentage of total RB6-$8C5^+$ ($8C5^+$), $CD3^+$, $B220^+$, $CD4^+$ or $CD8^+$ cells that were of donor origin. The results are presented as the mean of 3 mice per group±SD.

DETAILED DESCRIPTION OF THE INVENTION

Figure 1A:
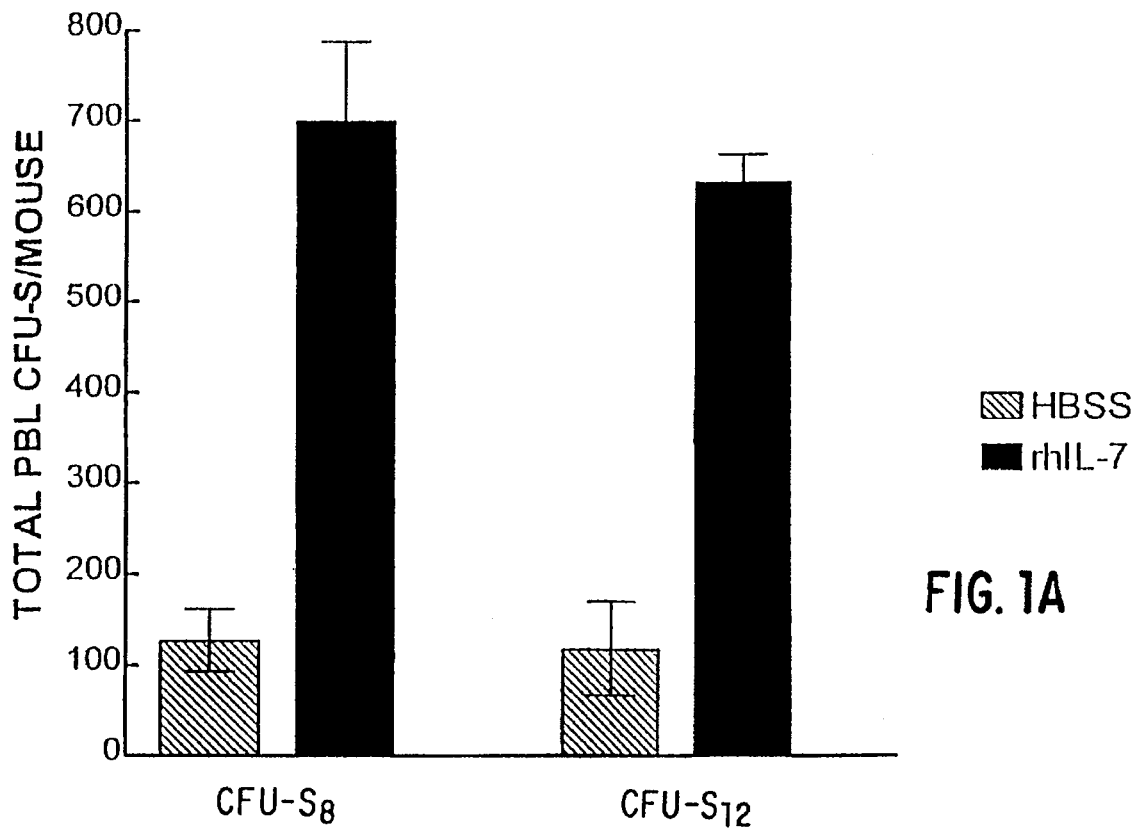
FIG. 1A shows the effect of systemic administration of rhIL-7 on progenitors for CFU-S in peripheral blood. The results are presented as the mean number from 3 mice per group (at each timepoint)±SD multiplied by the total number of cells obtained from donors and divided by $2\times10^5$ (the number of cells plated).

The present invention provides a method of isolating an increased number of hematopoietic stem cells from a subject comprising a) administering interleukin-7 (IL-7) to the subject in an amount that mobilizes the hematopoietic stem cells to the peripheral blood; and, b) isolating a population of leukocytes enriched for hematopoietic stem cells from the peripheral blood.

By "isolating a population of leukocytes enriched for hematopoietic stem cells from the peripheral blood" is meant removing peripheral blood from the subject wherein the number of hematopoietic stem cells in the peripheral blood has been increased, or enriched, by the administration of IL-7. This peripheral blood can then be further concentrated for hematopoietic stem cells as described below.

An example of effective IL-7 administration is given for mice in Examples I and II, and for humans in Example III. Generally, IL-7, including effective analogues having the relevant bioactive properties of IL-7, may be administered orally, parenterally (e.g., intravenously), by intramuscular injection, by intraperitoneal injection, topically, transdermally, or the like, although intravenous or subcutaneous administration is typically preferred. The exact amount of such IL-7 required will vary from subject to subject, depending on the species, age, weight and general condition of the subject, the particular mode of administration, and the like. Thus, it is not possible to specify an exact amount. However, an appropriate amount may be determined by one of ordinary skill in the art using only routine experimentation given the teachings herein. Generally, dosage will approximate that which is typical for the administration of cytokines. More specifically, to mobilize hematopoietic stem cells in a subject, 50 to 800 μg of IL-7 per subject kg, or more preferably 100 to 500 μg IL-7 per subject kg, can be administered. This administration is typically daily up to, or in some cases exceeding, 20 days, or preferably up to 7 days. Several cycles of IL-7 administration can be employed to allow several isolations of stem cells.

Depending on the intended mode of administration, the compounds of the present invention can be in pharmaceutical compositions in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. Typically, the protein will be in a liquid. In a preferred embodiment, the protein is lyophilized and diluted with a liquid carrier just prior to administration. The compositions will include, as noted above, an effective amount of the protein in combination with a pharmaceutically acceptable carrier and, in addition, may include other medicinal agents, pharmaceutical agents, carriers, adjuvants, diluents, etc. By pharmaceutically acceptable it is meant a material that is not biologically or otherwise undesirable, i.e., the material may be administered to an individual along with the protein without causing any undesirable biological effects or interacting in a deleterious manner with any of the other components of the pharmaceutical composition in which it is contained.

For solid compositions, conventional nontoxic solid carders include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc. an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Because IL-7 is a protein, if it is to be administered orally, it is preferred to encapsulate the protein to avoid its denaturation in the stomach. Actual methods of preparing such dosage forms are known, or will be apparent, to those skilled in this art; for example, see *Remington's Pharmaceutical Sciences*.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

The method of isolating an increased number of hematopoietic stem cells is practical for a variety of presently available uses immediately recognizable to one skilled in the art. For example, one could use the method for isolating a population of leukocytes enriched for hematopoietic stem cells which can then be used for therapeutic administration to an individual in need of such a population of cells. Such an individual may be in need of such mobilized hematopoietic stem cells due to a naturally occurring immunodeficient disease state, such as human immunodeficiency virus (HIV) infection, severe combined immunodeficiency disease (SCID) or cancer. Such an individual may be in need of such cells due to an intentionally induced immunodeficient state, such as from chemotherapy or irradiation. The method of isolating an increased number of hematopoietic stem cells can also be used to improve a transplantation of hematopoietic cells from a donor to a recipient, as in an autologous or allogenic transplant of peripheral blood or hematopoietic stem cells isolated from the peripheral blood. In the case of an autologous transfer, purification of the peripheral blood to concentrate hematopoietic stem cells has the advantage of removing cancer cells, among others, which would otherwise be reintroduced into the patient.

Furthermore, the method of isolating an increased number of hematopoietic stem cells provides an immediately available use as a research tool for the study of hematopoietic stem cells. For example, by practicing the methods herein one is able to predictably mobilize hematopoietic stem cells into the peripheral blood where they can be harvested in a population of leukocytes. The isolated population of leukocytes enriched for hematopoietic stem cells can then be used to test the effects of various compounds, such as growth factors, on the hematopoietic stem cells. By providing such a method of obtaining hematopoietic stem cells, skilled researchers can use the presently available cells to elucidate additional curative therapies for disease. Additionally, the hematopoietic stem cells can be used to provide a vector for the transfer of genetic material to a lineage of long term repopulating hematopoietic cells.

The invention also provides a method of transplanting an increased number of hematopoietic stem cells from a donor to a recipient to enhance repopulation of the recipient's hematopoietic and immune cells comprising a) administering interleukin-7 to the donor in an amount that mobilizes the hematopoietic stem cells to the peripheral blood; b) isolating a population of leukocytes from the donor's peripheral blood that has been enriched for hematopoietic stem cells by the interleukin-7 administration; and, c) transplanting the isolated population of leukocytes enriched for hematopoietic stem cells to the recipient, thereby enhancing the repopulation of the recipient's hematopoietic and immune cells. An example of this method is provided in Example I.

The method of transplanting an increased number of hematopoietic stem cells from a donor to a recipient contemplates autologous and allogenic hematopoietic stem cell transplantations. Thus, in the case of autologous transplants, the donor is also the recipient, and vise versa. The method is intended to enhance repopulation of the recipient's hematopoietic and immune cells, in part, by the increased number of hematopoietic stem cells given to the recipient. The amount of IL-7 to be administered is generally within the ranges described above for stem cell mobilization. 50 to 800 µg of IL-7 per donor kg, or more preferably 100 to 500 µg IL-7 per donor kg, can be administered daily up to, or in some cases exceeding, 20 days, or preferably, 7 days. Several cycles of IL-7 administration can be employed to allow several isolations of peripheral blood cells enriched for stem cells.

The number and concentration of isolated leukocytes enriched for hematopoietic stem cells to be transplanted can vary according to the discretion of the skilled artisan. The protocol and technical considerations for the transplantation of such mobilized hematopoietic stem cells from the peripheral blood of a human recipient to a human donor is generally given in Example III.

Generally, in a human subject, one would attempt to transplant at least 2 to $8 \times 10^8$ peripheral blood leukocytes per recipient kilogram. In addition to IL-7 administration sufficient for hematopoietic stem cell mobilization, the peripheral blood cells can be further increased or enhanced in the donor prior to harvesting. Such additional methods for increasing the number of stem cells in the peripheral blood of humans are given in Example III. For example, such an induction therapy can be a non-lethal chemotherapy, which stimulates a rebound and over production of peripheral blood leukocytes, or treatment regimens with various colony stimulating factors and cytokines.

Furthermore, the hematopoietic stem cells can also be concentrated from the peripheral blood cells after harvesting from the donor and before transplantation in the recipient by a variety of techniques. For example, the peripheral blood cells may be concentrated for hematopoietic stem cells by centrifugation, counter-current elutriation, selection with $CD34^+$ or stem cell related antibodies, or removal of lineage positive (committed) hematopoietic cells. Such methods are well-known in the art. See e.g., U.S. Pat. Nos. 5,061,620; 5,087,570; 5,061,620; 4,714,680; 4,965,204; and 5,035,994. See Example III for representative details. Because these methods increase the relative concentration of stem cells in relation to other cells in the peripheral blood, fewer peripheral blood leukocytes can beadministered effectively.

The invention also provides a method of improving engraftment of a bone marrow transplant or a peripheral blood leukocyte transplant from a donor to a recipient comprising administering interleukin-7 to the recipient following transplantation in an amount that enhances engraftment. Engraftment can include lymphoid reconstitution, myeloid reconstitution or both. An example of this method can be found in Example II.

The method of improving engraftment of a bone marrow transplant or a peripheral blood leukocyte transplant contemplates autologous and allogenic transplantations. Thus, in the case of autologous transplants, the donor is also the recipient, and vise versa. The amount of bone marrow to be transplanted can vary according to the discretion of the skilled artisan. The protocol and practical considerations for a human bone marrow transplant in humans are generally given in Example III. The amount of IL-7 to be administered to the recipient is within the ranges described above for stem cell mobilization. About 50 to 800 µg of IL-7 per donor kg, or more preferably 100 to 500 µg IL-7 per donor kg, can be administered per day, however, the administration of such amounts will vary according to the standards set forth by clinicians in the field of transplantation enhancement therapy. Administration should occur daily following the bone marrow transplantation for 1 or more days, preferably daily or intermittently for up to 200 days.

As used herein "a" or "an" means one or more than one, depending upon the context within which it is used. Certain publications are referred to herein, and are hereby incorporated by reference in their entirety. The following examples are provided for illustration of some embodiments of the invention and are not in any way intended to limit the invention to those particular embodiments. The described and other embodiments of the present invention will be apparent to one with skill in the art.

EXAMPLE I

*Mice.* C57BL/6 (Ly 5.2) and their congenic C57BL/6-Ly 5.1 mice (12) were obtained from the Animal Production Area of the National Cancer Institute-Frederick Cancer Research and Development Center (Frederick, Md.), maintained in a specific pathogen-free environment, and used between 8–10 weeks of age.

*Reagents.* RhIL-7 was purchased from PeproTech (Rocky Hill, N.J.), and had a specific activity of $2\times10^7$ U/mg as measured by proliferation of a murine pre-B-cell line (IxN/A6). The endotoxin level was less than 0.1 ng/ml. Lyophilized material was diluted in titrate buffer pH=6.0 to a concentration of 1 mg/ml. Mice received injections of rhIL-7 or diluent (Hanks' Balanced Salt Solution [HBSS] without $Ca^{2+}$, $Mg^{2+}$ and phenol red [Cellgro, Washington, D.C.], supplemented with 0.1% normal mouse serum [NMS]).

*Enrichment and purification of peripheral blood leukocytes (PBL).* Peripheral blood from C57BL/6-Ly 5.1 mice that had been treated with 5 µg of rhIL-7 or diluent BID for 7 days (d) was collected by cardiac puncture and placed into EDTA-containing robes. Blood was pooled by group, layered over Lymphocyte Separation Media gradients of 1.077–1.080 g/ml (Organon Teknika, Durham, N.C.) and centrifuged at 800 xg for 20 min at 20° C. Low density (LD) PBL from the interface were collected, washed, resuspended in plain HBSS, and then used for transplantation.

*Preparation of bone marrow, spleen cells and thymocytes.* Bone marrow (BM) from both femurs and tibiae, spleen cells and thymocytes were isolated from recipient mice (6, 7, 13) and resuspended in HBSS+1% BSA (Gibco/BRL, Grand Island, N.Y.) for FCA. BM cells used for transplantation were resuspended in cold HBSS.

*Transplantation.* C57BL/6 (Ly 5.2) recipient mice were exposed to a total of 11.0 $Gy^{137}$Cesium irradiation (dose rate - 23.2 cGy/min) delivered in two equal doses of 5.5 Gy given 3 hours (h) apart. The CFU-S assay was performed by the i.v. injection of $2\times10^5$ LD PBL or BM cells from rhIL-7-treated or HBSS-treated C57BL/6-Ly 5.1 donor mice into irradiated recipients. On d 8 and 12 after transplantation, the number of macroscopically visible surface colonies (CFU-S) on fixed spleens was counted (14). Long term survival and reconstitution studies were done by injecting various numbers of LD PBL or BM cells from rhIL-7-treated or HBSS-treated C57BL/6-Ly 5.1 donors i.v. into lethally irradiated C57BL/6 (Ly 5.2) recipients.

*Surface phenotype analysis.* Hematopoietic reconstitution was determined by 2-to 3-color immunofluorescence labeling followed by flow cytometric analysis (FCA) (6). Donor derived (Ly $5.1^+$) or host-derived (Ly $5.2^+$) cells were detected using the mAb clones A-20-1.7 or 104-2.1 (15), respectively, and developed with FITC-conjugated affinity-purified goat anti-mouse $IgG_{2a}$. (Fisher Scientific, Orangeburg, N.Y.) or they were biotinylated and developed with STREPTAVIDIN-$RED_{670}$ (a fluorochrome-labeled avidin) (Gibco BRL, Life Technologies, Inc., Gaithersburg, Md.). B-lineage cells and granuloeytes were detected using PE-conjugated RA3-6B2 (B220) or PE-conjugated RB6-8C5, respectively (PharMingen, San Diego, Calif.). $CD4^+$ or $CD8^+$ T-lineage cells were detected using PE-conjugated GK 1.5 (L3T4) or biotin-conjugated 53-6.7 (Ly 2) developed with STREPTAVIDIN-$RED_{670}$, respectively (Beeton Dickinson, San Jose, Calif.). T cells were detected using 500A2 (CD3) as previously described (6).

*Statistical analysis.* All statistical evaluations were performed using the computer software; Instat ver. 2.02 or GRAPHPAD PRISM for Windows ver 1.0 (GRAPHPAD Software, San Diego, Calif.). GRAPHPAD PRISM is a statistical analysis software program. Statistically significant differences based on absolute numbers were determined by two-tailed, Student's t-test (16). Results from survival experiments were analyzed by logrank nonparametric test and expressed as Kaplan-Meier survival curves.

Figure 1B:
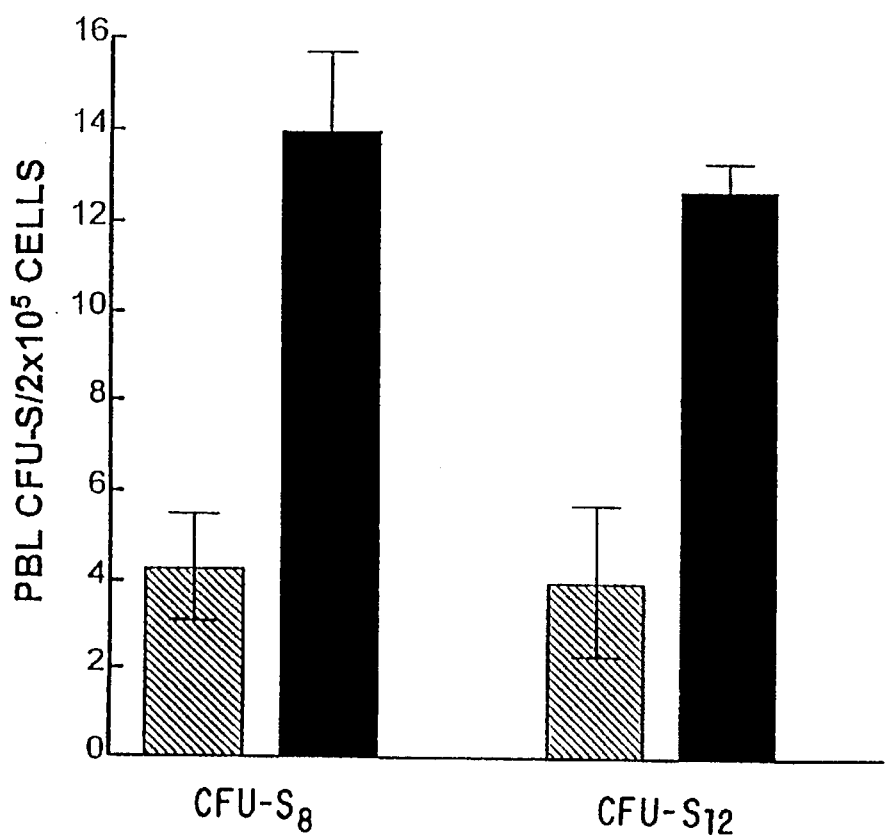
FIG. 1B shows the effect of systemic administration of rhIL-7 on progenitors for CFU-S in peripheral blood. The results are presented as the frequency of CFU-S obtained per $2\times10^5$ injected PBL.

FIGS. 1A and 1B show the effect of systemic administration of rhIL-7 on progenitors for CFU-S in peripheral blood. Lethally irradiated recipient mice (n=6) were injected i.v. with $2 \times 10^5$ PBL obtained from rhIL-7 (5 µg/BID for 7 d) or HBSS-treated (control) mice. After 8 and 12 d, mice were euthanized, and colonies on the surface of the spleens were counted. The results are presented as the mean number from 3 mice per group (at each timepoint)±SD multiplied by the total number of cells obtained from donors and divided by $2 \times 10^5$ (the number of cells plated) (FIG. 1A) or as the frequency of CFU-S obtained per $2 \times 10^5$ injected PBL (FIG. 1B).

Figure 2A:
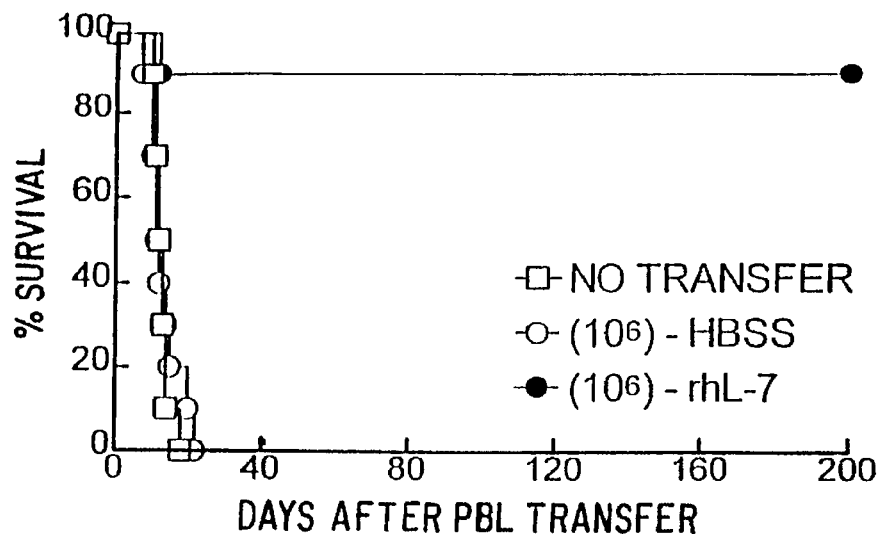
FIG. 2A shows the survival of lethally irradiated recipients (Ly 5.2) transplanted with $10^6$ PBL isolated from donors (Ly 5.1) treated with rhIL-7 or HBSS. The results are presented as a Kaplan-Meier survival curve.
Figure 2B:
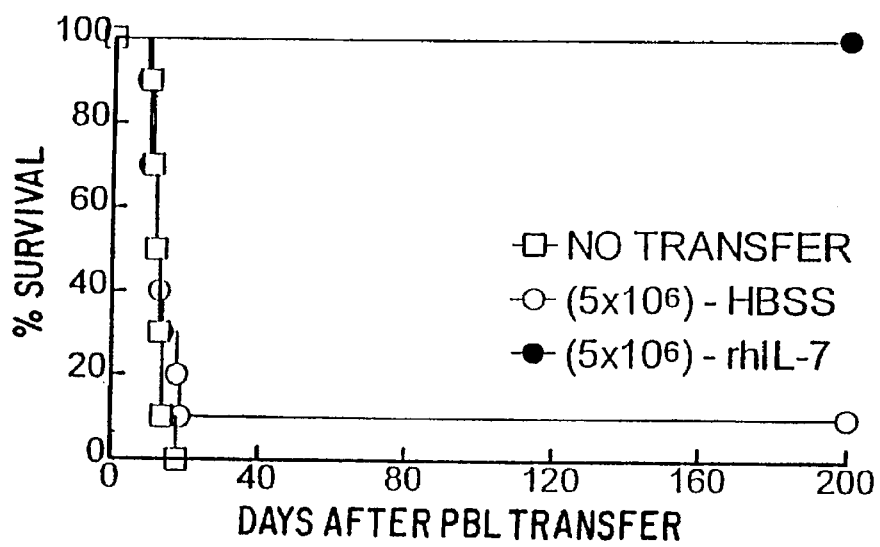
FIG. 2B shows the survival of lethally irradiated recipients (Ly 5.2) transplanted with $5\times10^6$ PBL isolated from donors (Ly 5.1) treated with rhIL-7 or HBSS. The results are presented as a Kaplan-Meier survival curve.
Figure 2C:
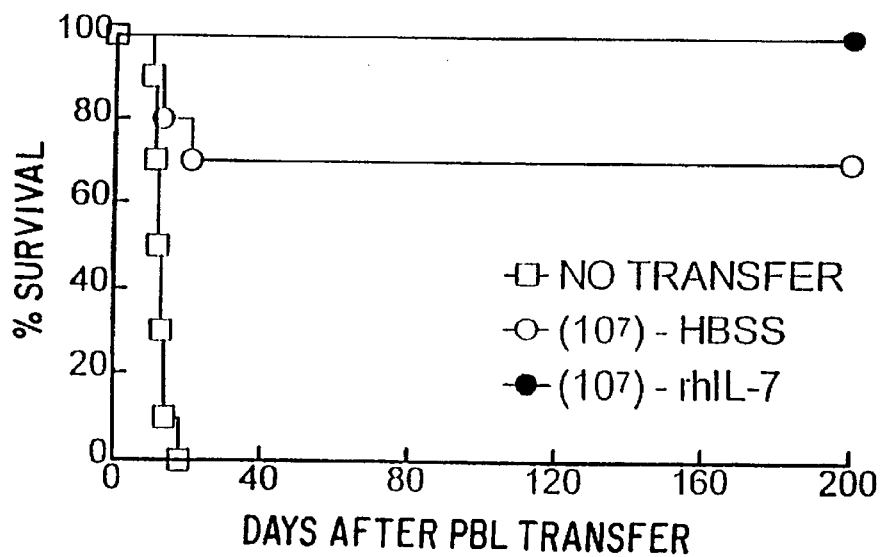
FIG. 2C shows the survival of lethally irradiated recipients (Ly 5.2) transplanted with $10^7$ PBL isolated from donors (Ly 5.1) treated with rhIL-7 or HBSS. The results are presented as a Kaplan-Meier survival curve.

FIGS. 2A, 2B and 2C show the survival of lethally irradiated recipients (Ly 5.2) transplanted with PBL isolated from donors (Ly 5.1) treated with rhIL-7 or HBSS. Lethally irradiated recipient mice (n=10) were injected i.v. with $10^6$, $5 \times 10^6$ or $10^7$ PBL from rhIL-7 (5 µg/BID for 7 d) or HBSS treated mice. The survival of mice was monitored for up to 200 d. The results are presented as a Kaplan-Meier survival curve.

FIGS. 3A and 3B show the percentage of donor cells (Ly 5.1$^+$) repopulating various organs of lethally irradiated recipient (Ly 5.2$^+$) mice transplanted with PBL and BMC from rhIL-7 or HBSS-treated donors. Lethally irradiated recipient mice (n=6) were injected i.v. with $10^6$ or $10^7$ PBL obtained from rhIL-7 (5 µg/BID for 7 d)-treated mice, $10^7$ of PBL from HBSS-treated mice (control) or with $10^6$ BM cells obtained from either treatment. At 3 and 6 mo after transplantation, 3 mice from each group were euthanized, and tibias, femurs, spleen and them were collected individually from each group. BMCs, thymocytes and splenocytes were isolated and counted. Cells were labeled with anti-Ly 5.1 or anti-Ly 5.2 to determine whether of donor or host origin as described above. The inset table (FIG. 3B) demonstrates multiple-lineage reconstitution determined by the percentage of total RB6-8C5$^+$ (8C5$^+$), CD3$^+$, B220$^+$, CD4$^+$ or CD8$^+$ cells that were of donor origin. The results are presented as the mean of 3 mice per group±SD.

*Administration of IL-7 increases the number of circulating CFU-S.* Lethally irradiated C57BL/6 (Ly 5.2) recipient mice were injected i.v. with $2 \times 10^5$ LD PBL or BM cells from rhIL-7 (5 µg i.p./BID for 7 d) or HBSS-treated C57BL/6-Ly 5.1 donors. A statistically significant increase in the total number of CFU-S$_8$ (p<0.001) and CFU-S$_{12}$ (p<0.001) was observed following transfer of PBL from mice treated with rhIL-7 (d8: 700±87, d12: 633±29) (FIG. 1A) compared with PBL from donors injected with HBSS (d8: 128±34, d12:118±51). Thus, in addition to its established ability to mobilize single-lineage CFU-c and multi-lineage CFU-GEMM (7), IL-7 mobilized primitive CFU-S from the bone marrow to the blood.

*PBL isolated from rhIL-7-treated donors rescue lethally irradiated mice.* To determine if rhIL-7 could mobilize pluripotent stem cells, lethally irradiated C57BL/6 (Ly 5.2) recipients were transplanted with various numbers of PBL from C57BL/6 (Ly 5.1 ) donors that were pretreated with rhIL-7 (5 µg/BID). As shown in FIG. 2A, $10^6$ PBL obtained from rhIL-7-treated donors rescued 90% of the irradiated recipients, while the same number of PBL isolated from control donors produced no survivors. A higher number of PBL ($5 \times 10^6$ and $\times 10^7$) transplanted from rhIL-7-treated donors rescued 100% of the recipients, while these cell doses of PBL from control mice were much less efficient ($5 \times 10^6$ - 10% and $1 \times 10^7$-70% see FIGS. 2B and 2C). These results demonstrated that PBL from rhIL-7-treated mice were much more efficient in long term rescue of irradiated recipients, suggesting the mobilization of pluripotent stem cells with long term marrow repopulating ability (LTMRA).

*PBL from mice treated with rhIL- 7 contain long term reconstituting stem cells that repopulate all leukocyte lineages in lethally irradiated recipient mice.* To determine if the rescue &lethally irradiated recipients by rhIL-7 mobilized PBL was associated with reconstitution by stem or progenitor cells transplanted from donor mice, the percentage of donor (Ly 5.1$^+$) vs host (Ly 5.2$^+$) repopulation in bone marrow, thymus and spleen of surviving recipient mice was assessed by FCA at 3 mo (short term repopulation) and 6 mo (long term repopulation). The analysis of data at 3 mo revealed that $10^7$ PBL from rhIL-7 treated donors reconstituted bone marrow, thymus and spleen cellularity to the same degree as did $10^6$ BM cells from control or rhIL-7-treated donors (Table 1). Analysis of short term host vs donor reconstitution in recipient mice transplanted with $10^7$ PBL from rhIL-7-treated donors (FIG. 3A; 3 mo) demonstrated that the majority of the cells in various organs were of donor origin (the % of donor Ly 5.1$^+$ cells ranged from 89 to >99). These percentages were significantly (p<0.001) greater than those obtained from reconstitution by $10^7$ PBL from control mice which showed only 8% donor reconstitution of the bone marrow and 5% donor reconstitution of the thymus in recipient mice. After 3 mo, reconstitution of the spleen with $10^7$ PBL was somewhat better (27±8%), but was still significantly lower than the reconstitution achieved by $10^6$ (p<0.05) or $10^7$ (p<0.001 ) PBL from rhIL-7 treated mice. Thus, the repopulation that occurred in the group that received $10^7$ PBL from control donors was largely of recipient origin by 3 mo. The transfer of $10^6$ PBL from rhIL-7-treated donors also resulted in better mean levels of % donor repopulation than did $10^7$ transferred normal PBL, but the variability was higher among the responding mice (FIG. 3A, 3 mo).

Because the 3-month survival assay is considered to be a good measurement for only short term repopulating stem cells (17), repopulation was also analyzed at 6 mo, which is the only way to measure repopulation by totipotential stem cells. As shown in Table 1, all of the recipients had considerable repopulation by 6 mo; however the reconstitution of the spleen by $10^7$ PBL from control mice was significantly lower (p<0.05) when compared with PBL ($10^7$) from the rhIL-7 treated mice and BM from normal or rhIL-7-treated mice. The percentages of donor cells in surviving mice at 6 mo were similar to that noted at 3 mo (FIG. 3A). The efficiency of overall donor-origin cell repopulation in some organs was less in mice that received $10^7$ PBL from control mice versus those that received $10^7$ PBL from rhIL-7-treated donors (BM: 4±1% vs 92±4%; thymus: 5±6% vs 98±1%; and spleen: 18±6% vs 94±1%). In fact, the efficiency of donor-origin cell repopulation by $10^7$ PBL from rhIL-7-treated donors was as good as that achieved by $10^6$ normal BM cells. Mice transplanted with $10^6$ PBL from rhIL-7-treated donors at 6 mo exhibited higher variability in terms of the percentage of donor cells for various organs (BM: 33±51%, thymus: 41±51%, spleen: 51±36%), but those mean percentages tended to be much higher than those attained by $10^7$ PBL from normal donors.

These results show that administration of rhIL-7 can mobilize progenitor and stem cells required for both short and long term repopulation. Successful repopulation with donor cells was dependent on the number of PBL transplanted, with a dose of $10^6$ from rhIL-7-treated donors being borderline for complete survival and repopulation of irradiated recipients, while $10^7$ PBL or $10^6$ BM cells were able to efficiently repopulate recipient mice. Interestingly, $10^7$ PBL from control donors also were able to rescue some mice for 6 mo, however, ultimately repopulation was largely of host origin. Thus, normal peripheral blood contains adequate numbers of short term repopulating cells (STRC) (18) to allow survival of irradiated mice; however, there are few long term repopulating cells (LTRC), which predominantly contribute to both 3-mo and 6-mo survival. The frequency of STRCs in normal PBL must be low since $10^6$ PBL from control mice failed to rescue any recipients. In fact, as shown in FIG. 1B, there were only 4±1 CFU-$S_g$ and 4±2 CFU-$S_{12}$ per $2 \times 10^5$ cells detected in the blood of control mice, whereas the rhIL-7 treated mice showed a significant increase (p<0.001) in the frequency of these progenitors (e.g. 14±2 CFU-$S_8$ and 13±1 CFU-$S_{12}$). This increase might contribute to the observation that 10-fold fewer PBL from IL-7-treated mice were able to fully rescue mice compared with PBL from normal mice. Although $10^6$ PBL from rhIL-7-treated donors and $10^7$ PBL from control mice were able to rescue the lethally irradiated recipients, only PBL from mice treated with rhIL-7 could successfully repopulate various organs with donor derived cells, further suggesting that PBL from control mice contain STRCs supporting early bone marrow recovery, followed by repopulation with host-originated LTRCs that survived irradiation. In contrast, PBL from rhIL-7-treated donors provide both STRCs for initial recovery and LTRCs that sustain long term hematopoiesis. This is further emphasized by the data shown in FIG. 3B, inset table, where complete trilineage (T and B cell, and myelomonocytic cell) reconstitution is demonstrated in various organs. A similar trend also was observed by 3 mo.

Interestingly, BM cells from rhIL-7-treated mice were almost equal to BM cells from control mice in repopulating ability. Our previously published results demonstrated that mature progenitors were reduced in BM from mice treated with rhIL-7 (CFU-C, and CFU-GEMM) (6, 7), suggesting that the ability of such bone marrow to repopulate lethally irradiated mice might also be diminished. The data presented herein suggest that at least some threshold number of short term and long term repopulating cells are retained in BM from rhIL-7-treated mice. This is in agreement to previous data that various progenitors detected by different colony forming assays do not always equate to an ability to reconstitute short and long term hematopoiesis in irradiated mice (19).

In summary, rhIL-7 has novel functions in vivo because of its unique combination of biological activities that include the ability to mobilize hematopoietic stem cells from the bone marrow to the periphery, its ability to accelerate regeneration of donor B and T lineages after transfer to irradiated hosts (See Example II), and documented potent effects on lymphocyte proliferation and T cell function (13). The mechanism of action for the stem cell mobilizing effects of rhIL-7, as for G-CSF and SCF, remains unknown and may be at least partially indirect through induction of other mobilizing cytokines (23) or through inhibition of negative regulators of hematopoiesis (24). rhIL-7, thus, appears to be useful for increasing the efficiency of stem cell mobilization into the peripheral blood for gene transfer studies, and for autologous or allogeneic stem cell transplants.

TABLE 1

Cellularity of various organs after reconstitution with PBL and BM from animals treated in vivo rhIL-7.

| Recipient Organ | Donor Cells | Cellularity ($\times 10^6$) 3 months/6 months |
|---|---|---|
| Bone Marrow | PBL ($10^7$ cells - HBSS) | 8 ± 3/17 ± 6 |
| | PBL ($10^6$ cells - rhIL-7) | 28 ± 1/22 ± 3 |
| | PBL ($10^7$ cells - rhIL-7 | 23 ± 6/22 ± 4 |
| | BM ($10^6$ cells - HBSS) | 16 ± 5/20 ± 6 |
| | BM ($10^6$ cells - rhIL-7) | 20 ± 4/21 ± 3 |
| Thymus | PBL ($10^7$ cells - HBSS) | 2 ± 2/23 ± 38 |
| | PBL ($10^6$ cells - rhIL-7) | 106 ± 17/24 ± 21 |
| | PBL ($10^7$ cells - rhIL-7 | 106 ± 8/37 ± 24 |
| | BM ($10^6$ cells - HBSS) | 80 ± 10/54 ± 9 |
| | BM ($10^6$ cells - rhIL-7) | 105 ± 10/65 ± 15 |
| Spleen | PBL ($10^7$ cells - HBSS) | 39 ± 32/42 ± 8 |
| | PBL ($10^6$ cells - rhIL-7) | 81 ± 11/52 ± 16 |
| | PBL ($10^7$ cells - rhIL-7 | 85 ± 2/77 ± 11 |
| | BM ($10^6$ cells - HBSS) | 74 ± 19/76 ± 8 |
| | BM ($10^6$ cells - rhIL-7) | 59 ± 6/65 ± 2 |

Lethally irradiated recipient mice (n = 6) were injected i.p. with $10^6$ or $10^7$ PBL obtained from rhIL-7 (5 µg/BID for 7d)-treated mice, $10^7$ PBL from HBSS-treated mice (control) or $10^6$ BM cells obtained after either treatment. At 3 and 6 mo after transplantation 3 mice from each group were euthanized and tibias, femurs, spleens and thymi were collected individually from each group. BMC, thymocytes and splenocytes were isolated as described in Materials and Methods and counted. The results are presented as the mean of 3 mice per group ± SD.

EXAMPLE II

*Mice.* Six to 10 week old female C57BL/6 (Ly 5.2) or C57BL/6-Ly 5.1 congenic mice were obtained and maintained as described in Example I.

*Cytokine treatment.* RhIL-7 generously supplied by Sterling Winthrop, he., Collegeville, Pa., had a specific biological activity of $2-5 \times 10^7$ units/mg, as measured by the proliferation of a murine pre-B cell line (31 ); the endotoxin levels were <2 endotoxin units/mg of rhIL-7. Mice were injected i.p. twice daily with HBSS containing 0.1% normal mouse serum (NMS) as a vehicle control or with 5 or 10 µg/injection of rhIL-7 in HBSS+0.1% NMS at 0.5 ml/injection. This regimen was based on observations from our previous studies (6, 13).

*Cell suspension preparation.* Bone marrow cells, splenocytes and thymocytes were prepared as previously described (6, 13). Erythrocytes in the bone marrow and splenocyte suspensions were rapidly lysed (5 seconds) with distilled water. Following a final wash with HBSS, the cells were either injected i.v. into irradiated recipients or labeled with antibodies for flow cytometric analysis (FCA).

*CFU-S assay.* The CFU-S assay was performed as described by Till & McCulloch (42). Briefly, 6-week old recipient mice were lethally irradiated (900 R) using a MARK 1 Irradiator affixed with a 302 attenuator (J. L. Shepherd, San Fernando, Calif.) containing a $^{137}$Cs source emitting 229 Rads (R)/minute, rested 3 to 4 hours, then reconstituted i.v. with $2 \times 10^5$ bone marrow cells or $5 \times 10^5$ splenocytes. Nine and 12 days later, their spleens were removed, fixed in Bouin's fixative, and scored for the presence of macroscopic colonies.

*Reconstitution assay.* Recipient mice were sublethally (750 R) or lethally (900 R) irradiated 3–4 hours before reconstitution. Recipients were injected i.v. with varying numbers of donor-origin bone marrow cells or splenocytes. At various times after reconstitution, the recipients were euthanized and their thymi and spleens were removed for further analysis. *Immunofluorescence labeling and flow cytometric analysis (FCA).* Three mice per group were used for each time point. Single-cell suspensions were labeled with antibody and FCA was performed as previously described (6). Donor- and host-origin cells were detected with the mAb reactive against Ly 5.1 (clone A-20-1.7; Ref. 15) and Ly 5.2 (done 104-2.1; Ref. 15), respectively, and developed with either FITC-conjugated affinity-purified goat anti-mouse IgG and IgM (H & L chain specific) antibody (Kirkegaard & Perry Laboratories Inc., Gaithersburg, Md.) for thymocytes or phycoerythrin-conjugated affinity-purified goat anti-mouse IgG2a (Caltag Laboratories, South San Francisco, Calif.) for splenocytes. Donor-origin splenic myeloid cells were detected in two-color analysis using the biotin-conjugated anti-granulocyte mAb clone RB6-8C5 (PharMingen, San Diego, Calif.) developed with Streptavidin-RED$_{613}$ (Gibco BRL, Life Technologies, Inc., Gaithersburg, Md.) combined with anti-Ly 5.1 mAb developed as indicated above. Donor-origin splenic T cells were detected in two-color analysis using the anti-CD3 monoclonal antibody 500A2 (43) developed with a FITC-conjugated affinity-purified goat anti-hamster IgG (H & L chain specific and mouse serum absorbed) antibody (Caltag Laboratories, South San Francisco, Calif.) combined with anti-Ly 5.1 mAb developed as indicated above. Donor-origin splenic B-lineage cells (B220$^+$) and mature B cells (surface Igμ$^+$) were detected in 3-color analysis using FITC-conjugated affinity-purified goat anti-mouse IgM (μ heavy chain specific) antibody (FisherBiotech, Fisher Scientific, Orangeburg, N.Y.) combined with phycoerythrin-conjugated anti-B220 mAb (clone RA3-6B2, PharMingen, San Diego, Calif.) and anti-Ly 5.1 mAb conjugated with biotin in our laboratory and developed with Streptavidin-RED$_{613}$. All antibodies used were titered to determine optimal working dilutions.

Figure 4:
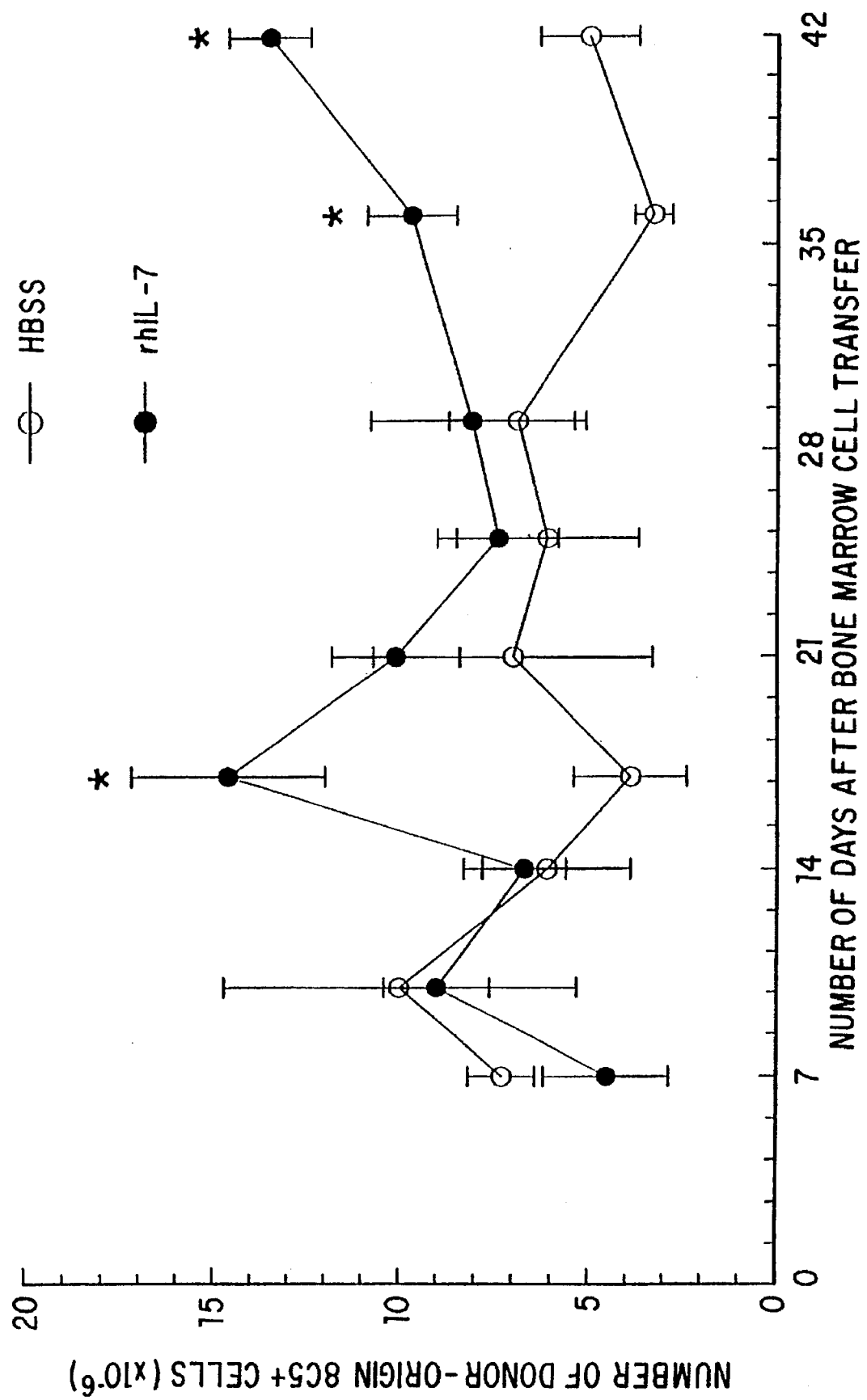
FIG. 4 shows that the administration of rhIL-7 to recipient mice given a bone marrow transfer results in minimal acceleration of donor-origin myeloid reconstitution.

FIG. 4 shows the administration of rhIL-7 to recipient mice given a bone marrow transfer results in minimal acceleration of donor-origin myeloid reconstitution. Lethally (900 R) irradiated C57BL/6 (Ly 5.2) recipient mice were injected i.v. with 10×10$^6$ bone marrow cells i.v. from C57BL/6-Ly 5.1 congertic mice. After cell transfer, recipients received HBSS+0.1% NMS (o) or 5 μg of rhIL-7 (●) i.p., twice a day throughout the course of the experiment. At varying times after transfer, the splenocytes from recipient mice were examined by FCA to determine the number of donor-origin myeloid cells using the anti-granulocyte mAb RB6-8C5. The data points indicate the mean±SD of 3 mice/group. Asterisks (*) indicate statistical significance; p<0.01 compared to HBSS for days 17 and 36 and p<0.001 for day 42.

Figure 5:
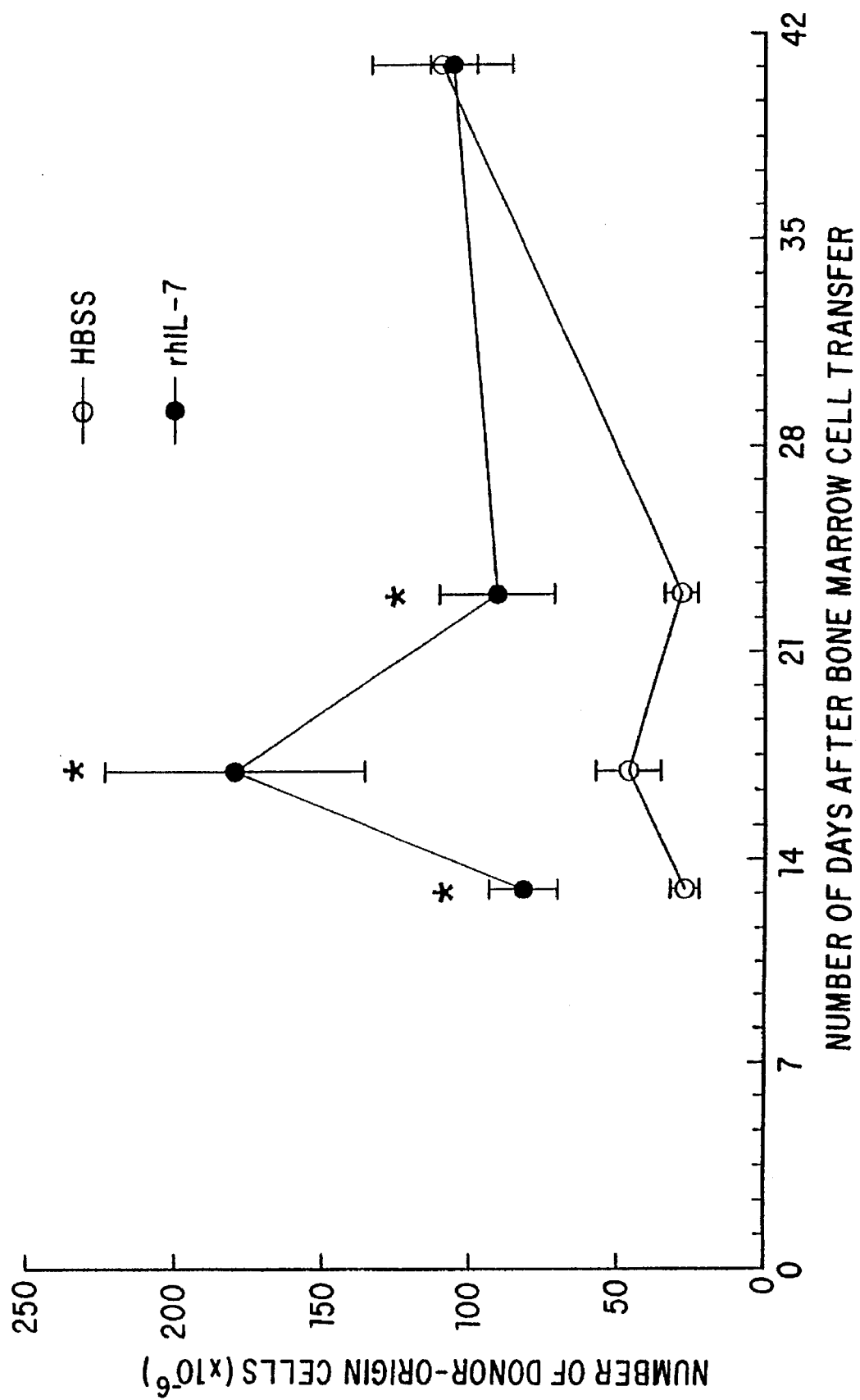
FIG. 5 shows that the administration of rhIL-7 to recipient mice given a bone marrow transfer results in accelerated reconstitution of donor-origin splenocytes.

FIG. 5 shows the administration of rhIL,-7 to recipient mice given a bone marrow transfer results in accelerated reconstitution of donor-origin splenocytes. In a similar experiment to that described in FIG. 4, the number of donor-origin cells (C57BL/6-Ly 5.1) contained in the spleens of recipient C57BL/6 (Ly 5.2) mice was quantitated by FCA at varying times after bone marrow transfer. Recipient mice that received HBSS+0.1% NMS or 5 μg of rhIL-7 are indicated by (o) or (●), respectively. The data points indicate the mean±SD of 3 mice/group. Asterisks (*) indicate statistical significance; p<0.01 compared to HBSS for days 13, 17 and 23.

Figure 6:
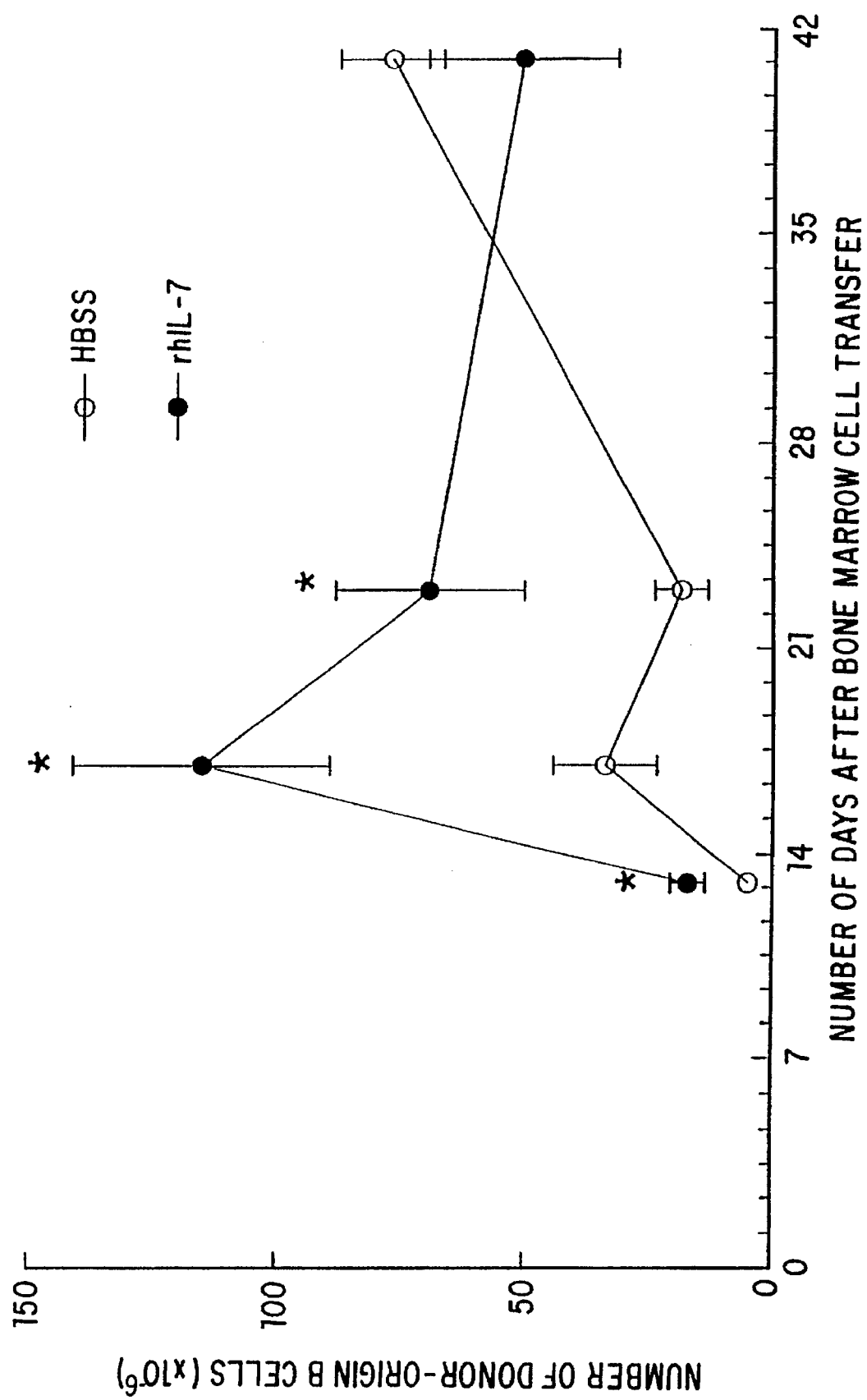
FIG. 6 shows that the administration of rhIL-7 to recipient mice given a bone marrow transfer results in accelerated reconstitution of donor-origin B cells.

FIG. 6 shows the administration of rhIL-7 to recipient mice given a bone marrow transfer results in accelerated reconstitution of donor-origin B cells. In the experiment described in FIG. 5, the splenocytes from recipient mice were examined by FCA to determine the number of donor-origin B cells. Recipient mice that received HBSS+0.1% NMS or 5 μg of rhIL-7 are indicated by (o) or (●), respectively. The data points indicate the mean±SD of 3 mice/group. Asterisks (*) indicate statistical significance; p<0.01 compared to HBSS for days 13 and 17 and p<0.02 for day 23.

Figure 7:
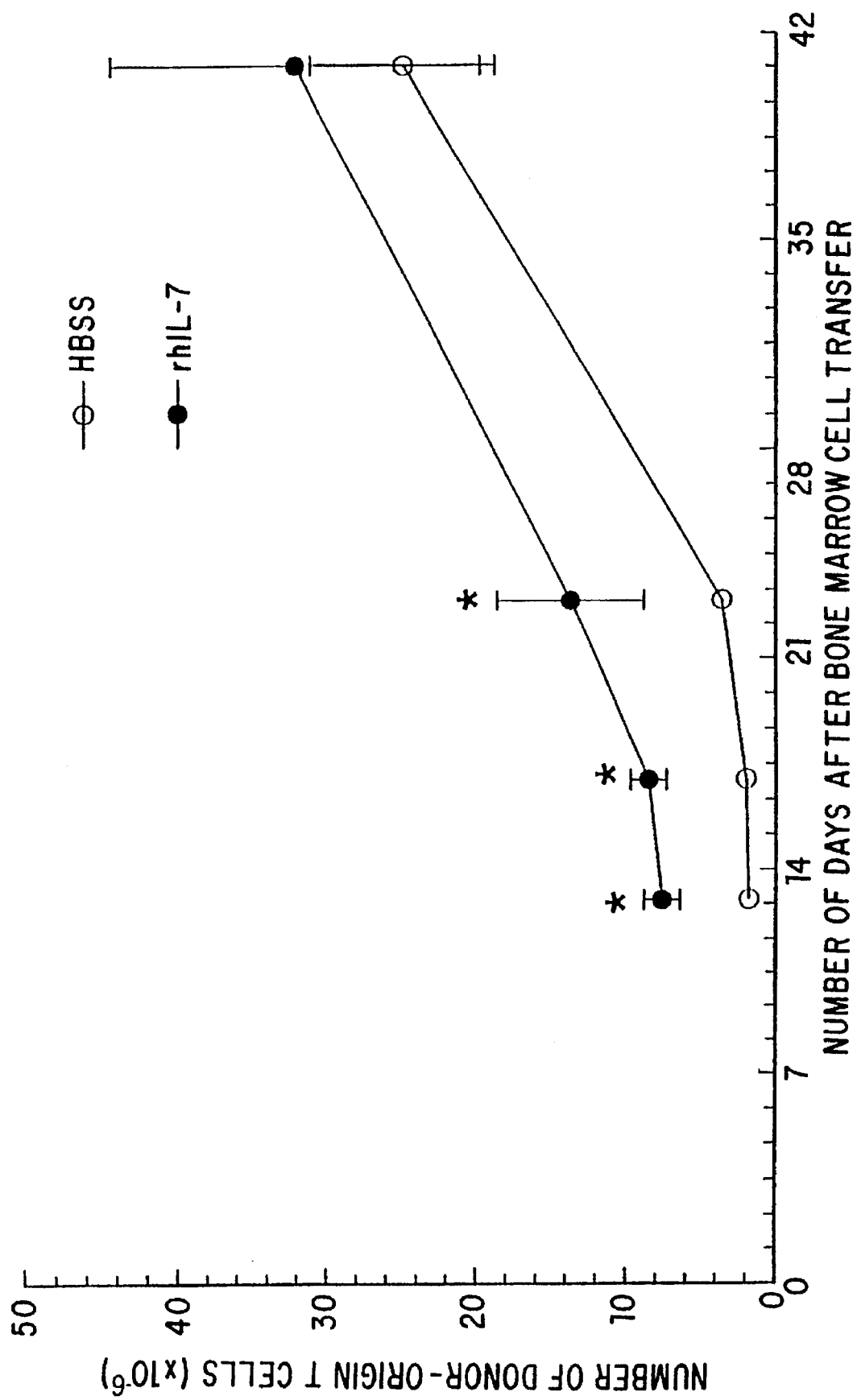
FIG. 7 shows that the administration of rhIL-7 to recipient mice given a bone marrow transfer results in accelerated reconstitution of donor-origin T cells.

FIG. 7 shows the administration of rhIL-7 to recipient mice given a bone marrow transfer results in accelerated reconstitution of donor-origin T cells. In the experiment described in FIG. 5, the splenocytes from recipient mice were examined by FCA to determine the number of donor-origin T cells at varying times after transfer. Recipient mice that received HBSS+0.1% NMS or 5 μg of rhIL,-7 are indicated by (o) or (●), respectively. The data points indicate the mean±SD of 3 mice/group. Asterisks (*) indicate statistical significance; p<0.01 compared to HBSS for day 13, p<0.001 for day 17 and p<0.05 for day 23.

*Effect of rhIL-7 on the frequency of CFU-S in bone marrow and spleen.* Previous work in our laboratory demonstrated that rhIL-7 administration to normal mice decreased the number of CFU-C and CFU-GEMM myeloid progenitors in the bone marrow and increased the number of these progenitors in the spleens by exportation from the bone marrow to the spleen (6, 7). To investigate the effect of rhIL-7 on even more immature erythro/myeloid progenitor and stem cells, the in vivo CFU-S assay was performed. Donor C57BL/6-Ly 5.1 mice were injected intraperitoneally (i.p.) with HBSS±0.1% NMS or 10 μg of rhIL-7 twice a day for 7 days. On the following day, 2 ×10$^5$ bone marrow cells or 5×10$^5$ splenocytes from these mice were injected i.v. into lethally irradiated (900 R) C57BL/6 (Ly 5.2) recipient mice. On days 9 or 12 after transfer, the spleens were removed from the recipient mice and CFU-S were enumerated. The results in Table 2 demonstrate that the number of CFU-S generated following transfer of BMC from rhIL-7-treated mice decreased in frequency by 7.5-fold (day 9) when compared to the numbers generated following injection of HBSS+0.1% NMS-treated control cells. However, the number of CFU-S generated following transfer of splenocytes from rhIL-7 treated mice increased in frequency by 4.3-fold (day 9) or 3.0-fold (day 12) when compared to the numbers generated following injection of HBSS+0.1% NMS treated control cells. Further, because of the ability of rhIL-7 treatment to significantly increase splenic cellularity (13) there was a 23.6-fold (day 9) or 15.5-old (day 12) increase in the CFU-S-generating capacity of splenocytes from rhIL-7-treated mice on a per organ basis (Table 2). Since rhIL-7 treatment does not decrease bone marrow cellularity (6), there was still a 3.4-fold (day 9) decrease in CFU-S-generating capacity in bone marrow on a per organ basis from rhIL-7 treated mice because of the decrease in frequency stated above.

*Lymphocyte regeneration following transfer of bone marrow cells or splenocytes from rhIL-7 treated mice into irradiated recipients.* To determine the effects of rhIL-7 on lymphoid progenitors in the bone marrow and spleen, sublethally (750 R) irradiated C57BL/6 (Ly 5.2) mice were injected i.v. with 5×10$^6$ bone marrow cells or 40×10$^6$ splenocytes from C57BL/6-Ly 5.1 mice that had been treated i.p. with HBSS+0.1% NMS or rhIL-7 (10 μg/injection) twice a day for 7 days. On day 15 after transfer, the thymi and spleens were removed from the recipients. The generation of donor-origin cells in the thymus and donor-origin B-lineage cells in the spleen was determined by FCA. The results in Table 3 demonstrate that the bone marrow from rhIL-7-treated mice had a 21-fold and 13.7- fold decrease in the frequency of precursors able to reconstitute the donor-origin thymocytes and B220$^+$ splenocytes, respectively, early after transfer when compared to cells from vehicle control treated mice. The fold-decrease in the relative number of precursors on a per organ basis in bone marrow from rhIL-7-treated mice compared to HBSS+0.1% NMS treated mice was similar (18.1-fold for thymocytes and 11.9-fold for B220$^+$ splenocytes).

In contrast, the reconstituting activity of splenocytes from rhIL-7 treated mice was not significantly different from splenocytes obtained from untreated mice in their ability to reconstitute the thymus of irradiated mice compared to controls when frequencies were compared. A decrease in frequency was observed in the ability of splenocytes from rhIL-7-treated mice to generate donor-origin B220$^+$ cells (2.4-fold) in the spleens of recipient mice compared to controls (Table 3). However, when the reconstituting ability of splenocytes from rhIL-7-treated mice was calculated on a per organ basis, as shown in Table 3, there was actually an increase in the ability of these splenocytes to reconstitute the thymus (4.0-fold), and B220$^+$ splenocytes (3.2-fold) when compared to the reconstituting ability of splenocytes from HBSS+0.1% NMS-treated control splenocytes.

*rhIL-7 accelerates lymphoid regeneration in lethally irradiated mice given a bone marrow transfer from normal mice.*
C57BL/6 (Ly 5.2) mice were lethally (900 R) irradiated and injected with 10×10$^6$ bone marrow cells from untreated C57BL/6-Ly 5.1 congenic mice. Following transfer, recipient mice were injected i.p. with HBSS+0.1% NMS or 5 μg of rhIL-7 twice a day throughout the course of the experiment. At varying times after transfer, recipient mice were examined by FCA to determine the amount of donor-origin myeloid reconstitution in the spleen. Administration of rhIL-7 resulted in a minor enhancement in myeloid reconstitution compared to bone marrow recipients treated with HBSS+0.1% NMS (FIG. 4).

In a similar experiment, FCA was used to determine the total number of donor-origin cells generated and further, the amount of donor-origin T-cell and B-cell reconstitution in the spleen. The generation of donor-origin splenocytes was accelerated in recipient mice that received rhIL-7 treatment (FIG. 5). Recipient mice treated with HBSS+0.1% NMS took up to 4 weeks longer to reach equivalent levels of reconstitution. Donor-origin subset analysis in the recipients' spleens was performed using FCA. Examination of donor-origin B-cell numbers in FIG. 6 and donor-origin T-cell numbers in FIG. 7 demonstrate that treatment of bone marrow recipient mice with rhIL-7 greatly enhanced the speed of reconstitution of both the B-cell and T-cell compartments by up to 4 weeks and 2 weeks, respectively, compared to bone marrow recipients treated with the vehicle control. CD4/CD8 analysis indicated that both the helper CD4$^+$ T cells as well as the cytotoxic CD8$^+$ T cells underwent this expansion (Table 4). However, administration of rhIL-7 appeared to preferentially expand the CD8$^+$ T cells, which we have previously described when normal mice are treated with rhIL-7 (8, 13).

The effects of rhIL-7 on lymphoid and myeloid progenitors, and on lymphoid- and myeloid-lineage repopulation were investigated using C57BL/6-congenic mice. rhIL-7 treatment markedly influenced the ability of bone marrow and spleen cells to generate CFU-S when transferred into irradiated recipients resulting in a 3.4-fold reduction or a 23.6-fold increase in the capacity of bone marrow or spleen cells, respectively, to form day 9 CFU-S generated from precursors thought to be committed to a particular lineage (44). Further, day 12 CFU-S generating capacity that arises from uncommitted precursors (44) was increased 15.5-fold in splenocytes from rhIL-7 treated mice. While previous data (6) demonstrated that localization of myeloid progenitors capable of generating CFU-c and CFU-GEMM is affected by rhIL-7 administration, the results presented here extend these observations to show that the numbers and localization of the earliest detectable erythro/myeloid progenitors also are affected by in vivo rhIL-7 treatment.

The results presented here are the first demonstration that rhIL-7 administration to mice also affects mobilization of lymphoid precursors and lymphopoiesis. Specifically, on a per organ basis, bone marrow from mice treated with rhIL-7 for 7 days had an 11.9-fold and a 18.1-fold decrease in the ability to reconstitute the B- and T-lineages, respectively, in irradiated recipients. However, the spleens from rhIL-7 treated mice, had a 3- to 4-fold increase in their ability to repopulate the lymphoid lineages. These effects were reversible and dependent on the length of rhIL-7 treatment. Thus, in vivo administration rhIL-7 significantly affects the localization and numbers of both lymphoid and myeloid precursors and, moreover, as shown in Example I, similar effects of rhIL-7 administration on the stem cell compartment occur as well. This unique combination of stem cell mobilization and more rapid lymphoid reconstitution distinguish the biological effects of IL-7 from the CSFs.

The mechanisms by which IL-7 exerts its effects are not clear, however the present data suggest that IL-7 may act (directly or indirectly) first by mobilizing precursor cells to extra-medullary sites. This hypothesis is supported by the substantial IL-7-induced reduction in precursor cells in the BM that coincide with an increase in those cells in the spleen. The second component of the IL-7-induced effect is likely due to induction of differentiation and expansion of the number of precursors that result in increased numbers of mature lymphoid- and myeloid-lineage cells.

Because IL-7 generated a leukocytosis in normal mice (13, 40) and accelerated lymphocyte repopulation in cyclophosphamide-treated mice (41) and sublethally irradiated mice (8) its potential application in accelerating myeloid and/or lymphoid reconstitution following bone marrow transplantation was studied in the C57BL/6 Ly 5-congenic mouse model. Lethally irradiated mice that had received normal donor-origin bone marrow cells and were treated with rhIL-7 had somewhat enhanced myeloid reconstitution in mice treated with rhIL-7. However, lymphoid reconstitution was both accelerated and enhanced for both donor-origin T cells and B cells. By 13 days after bone marrow transfer, there was a 3.4-fold increase in B-cell reconstitution in recipients treated with rhIL-7 compared to those that had received only HBSS+0.1% NMS. There was also, a 4-fold increase in the number of T cells generated in recipient mice treated with rhIL-7 compared to controls until at least the third to fourth week after transfer when reconstitution oft cells in control mice began to approach that of the rhIL-7-treated group. Further, there was no observable toxic effect of long-term (6 weeks) rhIL-7 treatment in these experiments unlike the study of Fraser et al. (45) in which 23% of lethally irradiated recipient mice that had received bone marrow infected with a retrovirus expressing the mIL-7 gene were moribund within 4–16 weeks after transplantation. These data illustrate that rhIL-7 administration is able to accelerate bone marrow engraftment following transplantation.

The results presented here demonstrate that IL-7 has potent effects on hematopoietic stem cell mobilization and accelerates bone marrow engraftment in lethally irradiated recipients. Thus, IL-7 administration is expected to enhance and accelerate lymphoid and myeloid regeneration in myeloablated cancer patients who receive BM transplants.

TABLE 2

Administration of rhIL-7 to mice alters the capacity of spleen and bone marrow cells to generate CFU-S.

| Donor Treatment - Organ | Cellularity of Donor Organ Following Treatment ($\times 10^{-6}$)[a] | # of Donor Cells Injected ($\times 10^{-5}$) | # of CFU-S/ Recipient d9 | # of CFU-S/ Recipient d12 | Total # of CFU-S Generated by Donor Cells on a Per Organ Basis[b] d9 | Total # of CFU-S Generated by Donor Cells on a Per Organ Basis[b] 12 |
|---|---|---|---|---|---|---|
| HBSS-BM | 14.6 | 2 | 15 ± 1 | 9 ± 3 | 1,080 ± 61 | 675 ± 201 |
| rhIL-7-BM | 32.0 | 2 | 2 ± 2[c] | 3 ± 3 | 320 ± 320[c] | 373 ± 403 |
| HBSS-Spleen | 49.6 | 5 | 3 ± 1 | 4 ± 1 | 278 ± 109 | 377 ± 129 |
| rhIL-7-Spleen | 252.0 | 5 | 13 ± 1[c] | 12 ± 2[c] | 6,552 ± 504[c] | 5,846 ± 982[c] |

Donor C57BL/6-Ly 5.1 mice (10 to 55 per group) were injected i.p. with HBSS + 0.1% NMS or 10 µg of rhIL-7, respectively, twice a day for 7 days. Following cessation of treatment, donor bone marrow (BM) cells or splenocytes were injected i.v. into 5 lethally (900R) irradiated C57BL/6 (Ly 5.2) recipients per group. On days 9 or 12 after transfer, the spleens were removed from the recipients and the number of CFU-S were enumerated. Lethally, irradiated recipient controls that were injected only with HBBS had no CFU-S on d 9 or d 12. Data represent the mean ± SD.
[a]Results indicate the number of cells from a pool of mice divided by the number of mice.
[b]These data were calculated by multiplying the number of CFU-S per recipient spleen by the total mean cellularity of the donor organ (column 2) and dividing by the number of donor cells injected.
[c]Significantly different from HBSS treated controls ($p < 0.001$).

TABLE 3

Administration of rhIL-7 to mice alters the capacity of spleen and bone marrow cells to regenerate lymphoid cells in irradiated recipients.

| Donor Treatment - Organ | Cellularity of Donor Organ Following Treatment ($\times 10^{-6}$)[a] | # of Donor Cells Injected ($\times 10^{-6}$) | # of Donor Thymocytes Generated/Thymus ($\times 10^{-6}$) | # of Donor B220+ Splenocytes Generated/Spleen ($\times 10^{-6}$) | Total # of Lymphoid Cells Generated by Donor Cells on a Per Organ Basis[b] Thymocytes ($\times 10^{-6}$) | Total # of Lymphoid Cells Generated by Donor Cells on a Per Organ Basis[b] B220+ Splenocytes ($\times 10^{-6}$) |
|---|---|---|---|---|---|---|
| HBSS-BM | 19 | 5 | 60.9 ± 19.1 | 59.1 ± 13.8 | 231.5 ± 72.7 | 244.4 ± 52.4 |
| rhIL-7-BM | 22 | 5 | 2.9 ± 3.5[e] | 4.3 ± 0.3[e] | 12.8 ± 15.5[e] | 18.9 ± 1.6[e] |
| HBSS-Spleen | 55 | 40 | 41.4 ± 19.6 | 14.9 ± 4.4 | 56.9 ± 26.9 | 20.4 ± 6.1 |
| rhIL-7-Spleen | 420 | 40 | 21.7 ± 9.4 | 6.3 ± 0.3[d] | 227.5 ± 98.5[d] | 65.8 ± 3.4[e] |

Donor C57BL/6-Ly 5.1 mice (5 to 25 per group) were treated as described in Table 2. Following treatment donor bone marrow (BM) or spleen cells were injected i.v. into sublethally (750R) irradiated C56BL/6 (Ly 5.2) recipients. Fifteen days after transfer the thymi and spleens from 3 mice/group were assayed using FCA to determine the number of donor-origina cells in the thymus or the number of donor-origin B220+ cells in the spleen of recipient mice. Data represents the mean ± SD.
[a]Results indicate the number of cells from a pool of mice divided by the number of mice.
[b]These data were calculated by multiplying the number of donor thymocytes or B220+ splenocytes per recipient spleen by the total mean cellularity of the donor organ (column 2) and dividing by the number of donor cells injected.
[c]Significantly different from HBSS treated controls ($p < 0.01$).
[d]Significantly different from HBSS treated controls ($p < 0.05$).
[e]Significantly different from HBSS treated controls ($p < 0.001$).

TABLE 4

Both CD4+ and CD8+ donor-origin T-cells expand in number in irradiated recipients following bone marrow transfer and rhIL-7 administration.

| Treatment of Recipient | Days After Transfer | # of Donor-Origin T-Cells per Subsets ($\times 10^{-6}$) CD4+ | # of Donor-Origin T-Cells per Subsets ($\times 10^{-6}$) CD8+ | CD4:CD8 Ratio |
|---|---|---|---|---|
| HBSS | 13 | 0.4 ± 0.1 | 0.7 ± 0.2 | 0.6:1 |
| rhIL-7 | 13 | 2.4 ± 0.6[a] | 4.7 ± 0.8[a] | 0.5:1 |
| HBSS | 17 | 0.9 ± 0.3 | 0.7 ± 0.1 | 1.3:1 |
| rhIL-7 | 17 | 2.9 ± 0.2[b] | 5.7 ± 0.9[b] | 0.5:1 |
| HBSS | 23 | 1.6 ± 0.3 | 1.3 ± 0.3 | 1.2:1 |
| rhIL-7 | 23 | 4.8 ± 1.1[a] | 7.0 ± 2.8[c] | 0.7:1 |
| HBSS | 41 | 17.5 ± 7.1 | 7.2 ± 1.7 | 2.4:1 |
| rhIL-7 | 41 | 16.7 ± 7.9 | 15.4 ± 6.7 | 1.1:1 |

Donor-origin splenic T cells shown in FIG. 4 were further analyzed by FCA to determine the number of cells contained in the CD4+ and CD8+ subsets. Data represent the mean ± SD of 3 mice/group.
[a]Significantly different from HBSS treated controls ($p < 0.01$).
[b]Significantly different from HBSS treated controls ($p < 0.001$).
[c]Significantly different from HBSS treated controls ($p < 0.05$).

EXAMPLE III

*Peripheral Stem Cell and Bone Marrow Transplantations in Humans.* The presently available use of peripheral stem cell transfer (PSCT) to transplant hematopoietic stem cells in humans has several advantages over the more generally practiced methods of autologous/allogeneic bone marrow transplantation (ABMT) (46, 47, 48). First, peripheral blood provides an alternative source for a hematopoietic graft for patients who are candidates for marrow ablative therapy and autologous rescue, but have a bone marrow abnormality that precludes ABMT. A number of bone marrow disorders have prompted the use of PSCT rather than ABMT. Hypocellularity and metastatic disease in the bone marrow are the most common abnormalities. Hypocellularity is usually the result of prior therapeutic irradiation in traditional marrow harvest sites or, less often, prior myelotoxic chemotherapy. Patients with hypocellular bone marrow have been treated with high-dose therapy and PSCT with good recovery of marrow function. Overt metastatic disease (more than 10% to 20% involvement as determined by light microscopic examination of bone marrow biopsies) in the bone marrow has been a relative contradiction to ABMT, but high-dose therapy and PSCT for patients with marrow metastasis has resulted in recovered hematopoiesis and, for some patients, long-term event-free survival.

Other disorders have prompted the use of PSCT including evidence of metastatic disease in the pelvic skeleton. Even though the bone marrow is not involved with such a tumor, the possibility that aspirating marrow through cancerous bone could contaminate the collection is a concern. Some centers prefer PSCT to ABMT if marrow metastases were ever documented in the patient's disease course, even though the marrow biopsy done just prior to stem cell procurement appears uninvolved with malignancy.

The second advantage PSCT can offer is a faster recovery of hematopoiesis following transplant (for some patients) than ABMT can provide. Rapid restoration of bone marrow function after PSCT occurs only if the transplanted stem cells are collected while their circulating numbers are intentionally increased. Mobilizing stem cells from extravascular sites into the circulation can be accomplished by the administration of myelosuppressive chemotherapy and/or hematopoietic growth factors. Currently, not every patient can experience a more rapid hematopoietic recovery following PSCT because mobilization attempts are not effective in all patients. Patients who are especially prone to fail mobilization attempts are those who have already received multiple courses of combination chemotherapy and those who have bone marrow metastases.

Peripheral stem cells may be preferable to bone marrow as an autograft product if, as has been hypothesized, an earlier reconstitution of immune function results after PSCT. This possibility has been considered because of the large number of immunocompetent cells (60% of circulating mononuclear cells are lymphocytes) that are in a peripheral stem cell graff product.

*Mobilization of Stem Cells in Preparation for PSCT.* Generally, IL-7 dosage will approximate that which is typical for the administration of cytokines, and will be in the range of about 2 µg/kg/day to 2 mg/kg/day. More specifically, to mobilize the hematopoietic stem cells of a human subject, 50 to 800 µg of IL-7 per subject kg, or more preferably 100 to 500 µg IL-7 per subject kg, can be administered per day over 1 to 7 days. Several cycles of IL-7 administration for 1 to 7 days, or longer, each can be employed to allow several isolations of stem cells.

*Enhanced Mobilization of Stem Cells in PSCT.* In addition to IL-7 administration, other stem cell inductive techniques may be used to enhance the mobilization of hematopoietic stem cells in the donor. For example, chemotherapy may be used in an induction therapy. About 16 days after chemotherapy is given (for example: single dose of Cy 4–7g/m$^2$), the number of circulating CFU-GM (single lineage myelomonocytic progenitors) increases about 14-fold above normal baseline values, and this increase persists for approximately 4 to 5 days. Additionally, hematopoietic growth factors (for example rhG-CSF) may be used in an induction therapy in humans. The drug is given by s.c. injections (10–30 µg/kg, or preferably 16 µg/kg) daily for 5 to 7 days. Leukapheresis is initiated 18 to 24 hours after the third dose of rhG-CSF and 4–7 doses is further administered. Each leukopheresis is performed 2 to 5 consecutive days. The leukopheresis product is cryopreserved in 12% DMSO and 20% autologous plasma using a controlled-rate liquid nitrogen freezer and stored in vapor phase of liquid nitrogen. This procedure yields an increase of WBC count from $4.8 \times 10^9$/L (range:3.2–8.4) before rhG-CSF, to a mean of $30.2 \times 10^9$/L (range 16.2–52.5) after 3 days of rhG-CSF administration and before the first leukapheresis. The absolute number of CD-34+cells per ml of blood increases 10-fold over baseline and peaks approximately on day 5 of G-CSF (48).

*Decreasing Myelosuppression of Non-Marrow Ablative Chemotherapy.* High doses of carboplatin can be used as a single agent for decreasing myelosuppression of 15 non-marrow ablative chemotherapy. Patients who entered the study received GM-CSF to facilitate hematopoietic recovery. Patients with disease that respond are eligible for a second course of therapy. The study can be modified to provide mobilized autologous peripheral stem cells along with GM-CSF after carboplatin administration. It has been suggested that the combination of peripheral stem cells and GM-CSF represent an effective method for delivering multiple cycles of high-dose chemotherapy.

*Processing, Cryopreservation, and Storage.* Apharesis collections have been prepared for cryopreservation without any additional manipulation but most often some method to remove contaminating red cells, granulocytes, or platelets is applied first (46, 47, 48). There are no known outward clinical consequences of the presence of platelets in the infused peripheral stem cell product. However, some centers perform a soft spin centrifugation of the product to remove platelets, which can then be returned to the patient to decrease the severity of thrombocytopenia associated with frequent multiple apheresis procedures. In contrast, the presence of granulocytes or red cells in the graft product can result in unwanted clinical toxicity, probably because these cells tend to lyse after cryopreservation and thawing. The hemoglobin and DNA released as a result of lysis is likely to be capable of producing renal and respiratory dysfunction. The number of high_density cells (red cells and granulocytes) can be reduced in the apheresis product by using one of several techniques including density gradients, counterflow centrifugation, and repeat apheresis. There is also limited success using CD34+ cells to induce a desirable cellular composition. They are usually used ex vivo to expand and mature cells into the myeloid lineage.

The two cryopreservation techniques used to maintain viability and peripheral stem cells while they are stored are essentially the same ones that have been used to preserve bone marrow (47). The most commonly used technique involves the use of dimethylsulfoxide (DMSO) as a cryoprotectant at a concentration of 10% by volume. The cell concentration adjusted with addition or removal of autologous plasma to about 1 to $2 \times 10^8$ cells/mL. The product is transferred to a specially designed freezing bag, and the bag is placed in an aluminum cassette. The product is cooled at a controlled rate until it reaches approximately $-85°$ C. Then, the cassette is stored in a liquid nitrogen freezer. An alternative method employs DMSO at a concentration of 5% by volume plus hydroxyethyl starch as the cryoprotectants. Rather than cooling the cells in a controlled rate freezer, they are placed in a $-80°$ C. freezer where they are both cooled (without rate control) and stored.

*Infusion of Stem Cells.* The patient is often given intravenous hydration for 2 hours or more prior to PSCT to encourage optimal renal function. Usually the cells are transported from the storage freezer to the patient's bedside, where the cells are thawed in a $37°$ to $40°$ C. water bath and immediately infused unfiltered through a central venous line. If the total volume of the graft product is extraordinarily large, 50% of the cells are given on the first day and the remaining 50% are given the second consecutive day; but typically all of the cells are infused over a 1- to 4-hour interval.

A number of side effects have been associated with infusion of thawed autologous peripheral stem cells. The development of hemoglobinuria is virtually inevitable, but it disappears without therapy in a day or two. Other common toxicities include nausea; vomiting, abdominal cramping, diarrhea, fever, chills, dyspnea, tachycardia, and headache. Generally, the number and severity of side effects increased with larger volumes of infusate and with greater red cell contamination of the graft product. Medicating patients with diphenhydramine hydrochloride and meperidine hydrochloride prior to the infusion seems to decrease the severity of the reactions.

*Stem Cell Harvest from Bone Marrow.* Bone marrow is first aspirated from both posterior iliac crest under general or regional anesthesia. The aspirated material is a mixture of marrow stem cells and contaminating peripheral blood. The mixture is anticoagulated with heparin, or anticoagulant titrate dextro se-NIH formula A. Approximately $2-5 \times 10^8$ nucleated bone marrow per kilogram are usually obtained, representing 5% of estimated total body marrow pool. After bone marrow harvest, hematopoiesis is virtually unaffected, except for a transient increase in erythropoiesis as a compensation for the loss of red blood cells. Most patients, however, have discomfort at the aspiration sites that persists for several days.

Whereas the unseparated marrow can be infused into patients without apparent adverse effects, development of stem cell processing steps have evolved to accomplish a variety of purposes:

| Aim | Method | Rationale |
| --- | --- | --- |
| Volume reduction | Centrifugation | Ease of storage and reinfusion |
| Plasma depletion | Centrifugation | ABO incompatibility, volume reduction |
| Erythrocyte depletion | Centrifugation, gradient isolation | ABO incompatibility, volume reduction |
| Granulocyte depletion | Centrifugation | Diminish transfusion reaction |
| Lymphocyte depletion | Elutriation; dexamethasone, antibody + complement, lectins, | Eliminate graft-versus-host disease |
| Malignant cell depletion | solid phase antibody Drugs, antibody + complement, LTMC | Eliminate tumor from autologous marrow |
| Stem Cell enrichment | Solid phase antibody | Improve engraftment |

*Combined Marrow and Peripheral Stem Cell Autotransplantation.* Administration of hematopoietic growth factors has shortened the duration of absolute neutropenia following high-dose therapy and ABMT but has had little effect on the duration of thrombocytopenia. Investigators have added autologous peripheral stem cells to a marrow autograft with the intent of hastening hematopoietic recovery following high-dose therapy. Clearly, the addition of non-mobilized peripheral stem cells has no effect on recovery rates. However, when mobilized peripheral stem cells, collected from previously untreated or minimally treated patients, are added to marrow autografts, the duration of both absolute granulocytopenia and thrombocytopenia is shortened. The number of reported combined autotransplants is small, but continued study in this area may demonstrate mobilized peripheral stem cells added to ABMT are more likely to promote platelet recovery following high-dose therapy than is the administration of currently available growth factors.

*Post-Transplantation Enhancement of Engraftment.* When one method of the present invention is practiced, IL-7 is administered to the bone marrow recipient or peripheral blood leukocyte recipient following transplantation in an mount that enhances engraftment. To mobilize the hematopoietic stem cells of a human recipient, 50 to 800 μg of IL-7 per subject kg, or more preferably 100 to 500 μg IL-7 per subject kg, can be administered daily for up to 200 days, or preferably for about 84 days.

Throughout this application various publications are referenced by numbers within parentheses. Full citations for these publications are as follows. The disclosures of these publications in their entireties are hereby incorporated by reference into this application in order to more fully describe the state of the art to which this invention pertains.

REFERENCES

1. Cheson, B. D., L. Lacerna, B. Leyland-Jones, G. Sarosy, and R. E. Wittes. 1989. Autologous bone marrow transplantation. Current status and future directions. Ann. Intern. Med 110:51.

2. To, L. B., M. L. Davy, D. N. Haylock, P. G. Dyson, D. Thorp, and C. A. Juttner. 1989. Autotransplantation using peripheral blood stem cells mobilized by cyclophosphamide. Bone Marrow Transplant. 4:595.

3. Briddell, R. A., C. A. Hartley, K. A. Smith, and .1. K. McNiece. 1993. Recombinant rat stem cell factor synergizes with recombinant human granulocyte colony-stimulating factor in vivo in mice to mobilize peripheral blood progenitor cells that have enhanced repopulating potential. Blood 82:1720.

4. Molineux, G., Z. Pojda, 1. N. Hampson, B. I. Lord, and T. M. Dexter. 1993. Transplantation potential of peripheral blood stem cells induced by granulocyte colony-stimulating factor. Blood 76:2153.

5. Gianni, A., M. Bregni, S. Siena, S. Villa, G. A. Sciorelli, F. Ravagvnani, G. Pellegris, and G. Bonadonna. 1989. Rapid and complete hemopoietic reconstitution following combined transplantation of autologous blood and bone marrow cells. A changing role for high dose chemo-radiotherapy. *Hematol. Oncol.* 7:139.

6. Damia, G., K. L. Komschlies, C. R. Faltynek, F. W. Ruscetti, and R. H. Wiltrout. 1992. Administration of recombinant human interleukin-7 alters the frequency and number of myeloid progenitor cells in the bone marrow and spleen of mice. *Blood* 79:1121.

7. Grzegorzewski, K., K. L. Komschiies, K. Kaneda, N. Usui, C. R. Faltynek, J. R. Keller, F. W. Ruscetti, and R. H. Wiltrout. 1994. Administration of recombinant human interleukin-7 to mice induces the exportation of myeloid progenitor cells from the bone marrow to peripheral sites. *Blood* 83:377.

8. Faltynek, C. R., S. Wang, D. Miller, E. Young, L. Tiberio, K. Kross, M. Kelley, and E. Kloszewski. 1992. Administration of human recombinant IL-7 to normal and irradiated mice increases the numbers of lymphocytes and some immature cells of the myeloid lineage. *J. Immunol.* 149:1276.

9. Jacobsen, F. W., 0. P. Veiby, C. Skjonsberg, and S. E. W. Jacobsen. 1993. Novel role of interleukin 7 in myelopoiesis: stimulation of primitive murine hematopoietic progenitor cells. *J. Erp. Med* 178:1777.

10. Takeda, S., S. Gillis, and R. Palacios. 1989. In vitro effects of recombinant interleukin 7 on growth and differentiation of bone marrow pro-B- and pro-T-lymphocyte clones and fetal thymocyte clones. *Proc. Natl. Acad Sci. USA.* 86:1634.

11. Park, L. S., D. J. Friend, A. E. Schmierer, S. K. Dower, and A. E. Namen. 1990. Murine interleukin 7 (IL-7) receptor. Characterization on an IL-7-dependent cell line. *J. Exp. Med.* 171:1073.

12. Morse, H. C., F. W. Shen, and U. Hammerling. 1987. Nomenclature for foci controlling mouse lymphocyte antigens. *Immunogenetics.* 23:71.

13. Komschlies, K. L., T. A. Gregorio, M. E. Gruys, T. C. Back, C. R. Faltynek, and R. H. Wiltrout. 1994. Administration of recombinant human IL-7 to mice alters the composition of B-lineage cells and T cell subsets, enhances T cell function, and induces regression of established metastases. *J. Immunol.* 152:5776.

14. Lord, B. I. 1993. In vivo assays for multipotential and marrow repopulating cells. In Haematopoiesis: A Practical Approach. N. G. Testa and G. Molineux, editors. Oxford University Press, Oxford. 1–19.

15. Shen, F. W. 1981. Monoclonal antibodies to mouse lymphocyte differentiation alloantigens. In Monoclonal Antibodies and T Cell. Hybridomas: Perspectives and Technical Advances. J. Hammerling, U. Hammerling, and J. F. Kearney, editors. Elsevier/North Holland and Biomedical Press, Amsterdam/New York/Oxford, 25–31.

16. Gosset, W. S. 1908. The probable error of the mean. *Biometrikca.* 6:1.

17. Jones, R. J., P. Cdano, S. J. Sharkis, and L. L. Sensenbrenner. 1989. Two phases of engraftment established by serial bone marrow transplantation in mice. *Blood* 73:397.

18. Ferrero, D., H. E. Broxmeyer, G. L. Pagliardi, S. Venuta, B. Lange, S. Pessano, and G. Rovera. 1983. Antigenically distinct subpopulations of myeloid progenitor cells (CFU-GM) in human peripheral blood and marrow. *Proc. Natl. Acad Sci. USA.* 80:4114.

19. Ploemacher, R. E. and N. H. C. Brons. 1989. Separation of CFU-S from primitive cells responsible for reconstitution of the bone marrow hemopoietic stem cell compartment following irradiation: Evidence for a pre-CFU-S cell. *Exp. Hematol.* 17:263.

20. Eaves, C. J. 1993. Peripheral blood stem cells reach new heights. *Blood* 82:1957.

21. Heyworth, C. M., S. J. Vailante, A. D. Whetton, and T. M. Dexter. 1990. The biochemistry and biology of the myeloid haemopoietic cell growth factors. *J. Cell. Sci. Suppl.* 13:57.

22. Tushinski, R. J., I. B. McAlister, D. E. Williams, and A. E. Namen. 1991. The effects of interleukin 7 (IL-7) on human bone marrow in vitro. *Exp. Hematol.* 19:749. 23. Alderson, M. R., T. W., Tough, S. F. Ziegler, and K. H. Grabstein. 1991. Interleukin 7 induces cytokine secretion and tumoricidal activity by human peripheral blood monocytes. *J. Exp. Med.* 173:923.

24. Dubinett, S. M., M. Huang, D. Dhanani, J. Wang, and T. Beroiza. 1993. Down-regulation of macrophage transforming growth factor β messenger RNA expression by IL-7. *J. Immunol.* 151:6670.

25. Balkwill FR, Burke F. (1989) The cytokine network. *Immunol. Today* 10:299–304.

26. Lee F. (1990) Growth factors controlling the development of hemopoietic cells. *Prog. Clin. Biol. Res.* 352:385–390.

27. Whitlock CA, Witte ON. (1982) Long-term culture of B-lymphocytes and their precursors from murine bone marrow. *Proc. Natl. Acad Sci. USA* 79:3608.

28. Whitlock CA, Robertson D, Witte ON. (1984) B cell lymphopoiesis in long term culture. *J. Immunol. Methods* 67:353–369.

29. Namen AE, Schmierer AE, March CJ, Overell RW, Park LS, Urdal DL, Mochizuki DY. (1988) B cell precursor growth-promoting activity. Purification and characterization of a growth factor active on lymphocyte precursors. *J. Exp. Med* 167: 988–1002.

30. Namen AE, Lupton S, Hjerrild K, Wignall J, Mochizuki DY, Schmierer A, Mosley B, March CJ, Urdal D, Gillis S, Cosman D, Goodman RG. (1988) Stimulation of B-cell progenitors by cloned murine interleukin-7. *Nature* 333:571–573.

31. Goodwin RG, Lupton S, Schmierer A, Hjerrild KJ, Jerzy R, Clevenger W, Gillis S, Cosman D, Namen AE. (1989) Human interleukin 7: molecular cloning and growth factor activity on human and murine B-lineage cells. *Proc. Natl. Acad. Sci. USA* 86: 302–306.

32. Lee G, Namen AE, Gillis S, Ellingsworth LR, Kincade PW. (1989) Normal B cell precursors responsive to recombinant murine IL-7 and inhibition of IL-7 activity by transforming growth factor-β[1] *J. Immunol.* 142, 3875–3883.

33. Cumano A, Dorshkind K, Gillis S, Paige CJ. (1990) The influence of S 17 stromal cells and interleukin 7 on B cell development. *Eur. J. Immunol.* 20, 2183–2189.

34. Conlon PJ, Morrissey PJ, Nordan RP, Grabstein KH, Prickerr KS, Reed SG, Goodwin R, Cosman D, Namen AE. (1989) Murine thymocytes proliferate in direct response to interleukin-7. *Blood* 74:1368–1373.

35. Okazaki H, Ito M, Sudo T, Hattori M, Kano S, Katsura Y, Minato N. (1989) IL-7 promotes thymocyte proliferation and maintains immunocompetent thymocytes bearing αβ and τδ T-cell receptors in vitro: synergism with IL-2. *J. Immunol.* 143: 2917–2922.

36. Everson MP, Eldridge H, Koopman WJ. (1990) Synergism of interleukin 7 with the thymocyte growth factors interleukin 2, interleukin 6 and tumor necrosis factor α in the induction of thymocyte proliferation. Cell. Immunol. 127:470–482.

37. Suda T, Murray R, Guidos C, Zlotnik A. (1990) Growth promoting activity of IL-1α, IL-6 and tumor necrosis factor-α in combination with IL-2, IL-4, or IL-7 on murine thymocytes. *J. Immunol.* 144:3039–3045.

38. Morrissey P J, Goodwin RG, Nordan RP, Anderson D, Grabstein KH, Cosman D, Sims J, Lupron S, Acres B, Reed SG, Mochizuki D, Eisenman J, Conlon PJ, Namen AE. (1989) Recombinant interleukin 7, pre-B cell growth factor, has costimulatory activity on purified mature T cells. *J. Exp. Med* 169:707–716.

39. Chazen GD, Pereira GMB, LeGros G, Gillis S, Shevach EM. (1989) Interleukin 7 is a T-cell growth factor. *Proc. Natl. Acad Sci. USA* 86:5923–5927.

40. Morrissey P J, Conlon P, Charder K, Braddy S, Alpert A, Williams D, Namen AIE, Mochizuki D. (1991) Administration of IL-7 to normal mice stimulates B-lymphopoiesis and peripheral lymphadenopathy. *J. Immunol.* 147:561–568.

41. Morrissey PJ, Conlon P, Braddy S, Williams DE, Namen AE, Mochizuki DY. (1991) Administration of IL-7 to mice with cyclophosphamide-induced lymphopenia accelerates lymphocyte repopulation. *J. Immunol.* 146:1547–1552.

42. Till JE, McCulloch EA. (1961) A direct measurement of the radiation sensitivity of normal mouse bone marrow cells. Radiat. Res. 14:213–222.

43. Allison IP, Havran WL, Poenie M, Kimura J, DeGraffenreid L, Ajami S, Duwe G, Weiss A, Tsien R. (1988) Expression and function of CD3 on murine thymocytes. In *The T-Cell Receptor, UCLA Symposia on Molecular and Cellular Biology, New Series, 73rd edition.* (Kappler J, Davis M, eds.) Liss, New York, N.Y., 33–45.

44. Spangrude GJ, Heimfeld S, Weissman IL (1988). Purification and characterization of mouse hematopoietic stem cells. *Science* 241:58–62.

45. Fraser CC, Thacker ID, Hogge DE, Fatur-Saunders D, Takei F, Humphdes RK. (1993) Alterations in lymphopoiesis after hematopoietic reconstitution with IL-7 virus-infected bone marrow. *J. Immunol.* 151: 2409–2418.

46. Meager RC, et al. (1993) Techniques of harvesting and cryopreservation of stem cells. *Hemat/Oncol Clin. of N. Amer.*, 7(3): 501–533.

47. Kessinger A. (1993) Utilization of peripheral blood stem cells in autotransplantation. *Hemat/Oncol Clin. of N. Amer.*, 7(3): 535–545.

48. Besinger J, et al. (1993) Autologous transplantation with peripheral blood mononuclear cells collected after administration of recombinant granulocyte stimulating factor. *Blood*, 81(11): 3158–3163.

What is claimed is:

1. A method of isolating an increased number of hematopoietic stem cells from a subject in need of an autologous transplant of hematopoietic stem cells comprising:
   a) administering interleukin-7 to the subject in an amount that mobilizes the hematopoietic stem cells to the peripheral blood; and
   b) isolating from the subject a population of leukocytes enriched for hematopoietic stem cells from the peripheral blood.

2. The method of claim 1, wherein 50 to 800 µg of interleukin-7 per kg of the subject is administered to the subject per day.

3. The method of claim 1, wherein 100 to 500 µg of interleukin-7 per kg of the subject is administered to the subject per day.

4. The method of claim 1, wherein interleukin-7 is administered to the subject daily for up to 20 days.

5. The method of claim 1, wherein interleukin-7 is administered to the subject daily for up to 7 days.

6. A method of transplanting an increased number of hematopoietic stem cells from a donor to a recipient to enhance repopulation of the recipient's hematopoietic and immune cells comprising:
   a) administering interleukin-7 to the donor in an amount that mobilizes the hematopoietic stem cells to the peripheral blood;
   b) isolating a population of leukocytes enriched for hematopoietic stem cells from the donor's peripheral blood; and,
   c) transplanting the isolated population of leukocytes enriched for hematopoietic stem cells to the recipient, thereby enhancing the repopulation of the recipient's hematopoietic and immune cells.

7. The method of claim 6, wherein 50 to 800 µg of interleukin-7 per kg of the donor is administered to the donor per day.

8. The method of claim 6, wherein 100 to 500 µg of interleukin-7 per kg of the donor is administered to the donor per day.

9. The method of claim 6, wherein interleukin-7 is administered to the donor daily for up to 20 days.

10. The method of claim 6, wherein interleukin-7 is administered to the donor daily for up to 7 days.

11. A method of improving engraftment of a bone marrow transplant from a donor to a recipient comprising administering interleukin-7 to the recipient following transplantation in an amount that improves engraftment.

12. The method of claim 11, wherein 50 to 800 µg of interleukin-7 per kg of the recipient is administered to the recipient per day.

13. The method of claim 11, wherein 100 to 500 µg of interleukin-7 per kg of the recipient is administered to the recipient per day.

14. The method of claim 11, wherein interleukin-7 is administered to the recipient daily for up to 200 days.

15. The method of claim 11, wherein interleukin-7 is administered to the recipient daily for up to 84 days.

16. A method of improving engraftment of a peripheral blood leukocyte transplant from a human donor to a human recipient in need of a peripheral blood leukocyte transplant comprising administering interleukin-7 to the recipient in need of a peripheral blood leukocyte transplant following transplantation in an amount that improves engraftment.

17. The method of claim 16, wherein 50 to 800 Bg of interleukin-7 per kg of the recipient donor is administered to the recipient per day.

18. The method of claim 16, wherein 100 to 500 µg of interleukin-7 per kg of the recipient is administered to the recipient per day.

19. The method of claim 16, wherein interleukin-7 is administered to the recipient daily for up to 200 days.

20. The method of claim 16, wherein interleukin-7 is administered to the recipient daily for up to 84 days.

* * * * *